United States Patent
Yao et al.

(10) Patent No.: US 11,672,506 B2
(45) Date of Patent: Jun. 13, 2023

(54) ULTRASOUND DIAGNOSIS APPARATUS AND IMAGE PROCESSING APPARATUS

(71) Applicant: Toshiba Medical Systems Corporation, Otawara (JP)

(72) Inventors: Cong Yao, Otawara (JP); Shintaro Niwa, Nasushiobara (JP); Tetsuya Kawagishi, Nasushiobara (JP); Yoshitaka Mine, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1341 days.

(21) Appl. No.: 14/560,581

(22) Filed: Dec. 4, 2014

(65) Prior Publication Data

US 2015/0087980 A1     Mar. 26, 2015

Related U.S. Application Data

(63) Continuation of application No. PCT/JP2013/065502, filed on Jun. 4, 2013.

(30) Foreign Application Priority Data

Jun. 5, 2012  (JP) .............................. JP2012-128247
Jun. 4, 2013  (JP) .............................. JP2013-118070

(51) Int. Cl.
*A61B 8/00* (2006.01)
*A61B 8/08* (2006.01)
(Continued)

(52) U.S. Cl.
CPC .............. *A61B 8/463* (2013.01); *A61B 8/467* (2013.01); *A61B 8/5246* (2013.01);
(Continued)

(58) Field of Classification Search
CPC ......... A61B 8/463; A61B 8/467; A61B 8/485; A61B 8/488; A61B 8/5246; A61B 8/5207;
(Continued)

(56) References Cited

U.S. PATENT DOCUMENTS

2003/0055336 A1*  3/2003  Buck ........................ A61B 8/06
                                                                 600/453
2006/0058624 A1    3/2006  Kimura
(Continued)

FOREIGN PATENT DOCUMENTS

CN    1775171 A    5/2006
JP    2-142551 A   5/1990
(Continued)

OTHER PUBLICATIONS

Machine translation of full document JP 09-135830; J-Plat Pat.*
Machine translation of full document JP 2008-272033; J-Plat Pat.*
Office Action dated Nov. 8, 2016 in Japanese Patent Application No. 2013-118070.
International Search Report dated Jul. 2, 2013 for PCT/JP2013/065502 filed on Jun. 4, 2013 with English Translation.
(Continued)

*Primary Examiner* — Sean D Mattson
(74) *Attorney, Agent, or Firm* — Oblon, McClelland, Maier & Neustadt, L.L.P.

(57) ABSTRACT

An ultrasound diagnosis apparatus according to an embodiment includes an obtaining unit, an image generating unit, and a controlling unit. The obtaining unit obtains setting information in which a plurality of types of ultrasound image data are set as display-purpose image data and in which a percentage of a time period to display the display-purpose image data is set for each of the plurality of types. The image generating unit generates, along a time series, each of the plurality of types of ultrasound image data set in the setting information. The controlling unit exercises control so that the plurality of types of ultrasound image data generated by the image generating unit are stored into a storage unit and exercises control so that the display-purpose
(Continued)

image data is displayed on a display unit according to the percentage set in the setting information for each of the types.

14 Claims, 13 Drawing Sheets

(51) Int. Cl.
  *G01S 15/89* (2006.01)
  *G01S 7/52* (2006.01)
  *A61B 8/14* (2006.01)

(52) U.S. Cl.
  CPC ...... *G01S 7/52036* (2013.01); *G01S 7/52038* (2013.01); *G01S 7/52042* (2013.01); *G01S 7/52071* (2013.01); *G01S 7/52074* (2013.01); *G01S 7/52085* (2013.01); *G01S 15/8979* (2013.01); *A61B 8/14* (2013.01); *A61B 8/485* (2013.01); *A61B 8/488* (2013.01); *A61B 8/5207* (2013.01); *A61B 8/5261* (2013.01); *A61B 8/54* (2013.01); *G01S 7/52022* (2013.01); *G01S 15/8915* (2013.01); *G01S 15/8963* (2013.01); *G01S 15/8993* (2013.01)

(58) Field of Classification Search
  CPC ......... A61B 8/5261; A61B 8/54; A61B 8/461; G01S 7/52036; G01S 7/52071; G01S 7/52074; G01S 15/8979
  See application file for complete search history.

(56) References Cited

U.S. PATENT DOCUMENTS

| | | | |
|---|---|---|---|
| 2007/0016029 A1* | 1/2007 | Donaldson | A61B 5/7475 600/437 |
| 2009/0012393 A1 | 1/2009 | Choi | |
| 2011/0270087 A1* | 11/2011 | Yoshida | A61B 8/06 600/443 |

FOREIGN PATENT DOCUMENTS

| | | |
|---|---|---|
| JP | H05-228153 A1 | 9/1993 |
| JP | 7-31608 A | 2/1995 |
| JP | H09-135830 A1 | 5/1997 |
| JP | H10-151131 A1 | 6/1998 |
| JP | 2004-113608 A | 4/2004 |
| JP | 2006-296495 A1 | 11/2006 |
| JP | 2008-142130 A1 | 6/2008 |
| JP | 2008-237909 A1 | 10/2008 |
| JP | 2008-272033 A1 | 11/2008 |

OTHER PUBLICATIONS

International Written Opinion dated Jul. 2, 2013 for PCT/JP2013/065502 filed on Jun. 4, 2013.

Combined Office Action and Search Report dated Sep. 30, 2015 in Chinese Patent Application No. 201380000675.X with English translation of categories of cited documents.

Office Action dated Jun. 13, 2017 in Japanese Patent Application No. 2013-118070.

\* cited by examiner

| B-MODE | 50% |
|---|---|
| COLOR DOPPLER MODE | 30% |
| ENHANCED MODE | 20% |

INTERPOLATED IMAGE DATA

INTERPOLATED IMAGE DATA

FIG.14A

| B-MODE | 40% |
|---|---|
| COLOR DOPPLER MODE | 20% |
| ELASTOGRAPHY MODE | 20% |
| ENHANCED MODE | 20% |

FIG.14B

| B-MODE | 50% |
|---|---|
| COLOR DOPPLER MODE | 25% |
| ELASTOGRAPHY MODE | 25% |

| ULTRASOUND IMAGE DATA | 50% |
|---|---|
| X-RAY CT IMAGE DATA | 30% |
| MRI IMAGE DATA | 20% |

| ULTRASOUND IMAGE DATA (fr:U) | X-RAY CT IMAGE DATA (fr:X) | MRI IMAGE DATA (fr:M) |
|---|---|---| ated in the ASQ mode (hereinafter,
ULTRASOUND DIAGNOSIS APPARATUS AND IMAGE PROCESSING APPARATUS

CROSS-REFERENCE TO RELATED APPLICATIONS

This application is a continuation of PCT international application Ser. No. PCT/JP2013/065502 filed on Jun. 4, 2013 which designates the United States, incorporated herein by reference, and which claims the benefit of priority from Japanese Patent Application No. 2012-128247, filed on Jun. 5, 2012, and Japanese Patent Application No. 2013-118070, filed on Jun. 4, 2013, the entire contents of which are incorporated herein by reference.

FIELD

Embodiments described herein relate generally to an ultrasound diagnosis apparatus and an image processing apparatus.

BACKGROUND

Ultrasound diagnosis apparatuses are configured to, by using an ultrasound probe that transmits and receives ultrasound waves, transmit ultrasound waves to a subject and receive reflective waves of the ultrasound waves reflected on an internal tissue of the subject. Further, the ultrasound diagnosis apparatuses are configured to generate an ultrasound image on the basis of reflected-wave signals (reception signals). Ultrasound diagnosis apparatuses are capable of generating ultrasound images having mutually-different characteristics by implementing various types (modes) of ultrasound wave transmitting/receiving methods and reception signal processing methods.

For example, when operating in a B-mode, an ultrasound diagnosis apparatus generates a B-mode image in which the strength of each reception signal is expressed by a degree of brightness. Such a B-mode image is used by an operator of the apparatus to understand features of a tissue structure serving as an observation target. As another example, when operating in a Doppler mode, an ultrasound diagnosis apparatus generates a color Doppler image, a power Doppler image, or the like, by utilizing changes in frequencies of transmission signals and reception signals. Such a color Doppler image and a power Doppler image are used by an operator of the apparatus to understand features of velocity information of a moving member (e.g., bloodstream) serving as an observation target.

As yet another example, when operating in an elastography mode, an ultrasound diagnosis apparatus measures hardness (elastic modulus) of an observation target by implementing an "autocorrelation method" or a "cross-correlation method" on reception signals and further generates an image (hereinafter, an "elasticity image") in which results of the measuring process are expressed. Such an elasticity image is used by an operator of the apparatus to understand the hardness of a tumor mass lesion site or the like serving as an observation target.

Further, ultrasound diagnosis apparatuses are also able to execute some other modes besides the modes described above. Examples of other modes include a mode in which microcalcification occurring in a tissue serving as an observation target is extracted from a B-mode image, so as to generate an image in which the extracted microcalcification is superimposed on the B-mode image. In the generated image, the microcalcification is enhanced (hereinafter, a "calcification enhanced image"). Another example of a mode which ultrasound diagnosis apparatuses are capable of executing is a mode in which a degree of deviation (a dispersion value) from a Rayleigh distribution of a signal amplitude distribution of reception signals is calculated by performing a statistical filtering process, so as to express the calculated dispersion value in an image. This mode may be referred to as an "Acoustic Structure Quantification (ASQ) mode". An image generated in the ASQ mode (hereinafter, a "statistical analysis image") is used by an operator of the apparatus to understand characteristics of a tissue serving as an observation target, e.g., a degree of fibrillization of the tissue.

Generally speaking, during an ultrasound examination, an image in one of a plurality of modes is taken at first. Alternatively, during an ultrasound examination, image taking processes in two modes may be performed at the same time, so that images in the two modes are displayed side by side or displayed in a superimposed manner. Further, when making an examination observation while using the image in the mode used at first or when performing an examination routine that is determined in advance, the operator manually switches the image taking mode to another mode.

In the conventional ultrasound examination described above, however, because the switching between the plurality of image taking modes is manually performed, a large burden is imposed on the operator. For example, because the switching between the modes is manually performed, there is a possibility that an image taking process in a mode that is optimal for making an image diagnosis of a certain disease may be missing from the procedure.

BRIEF DESCRIPTION OF THE DRAWINGS

FIG. 14A and FIG. 14B are drawings for explaining the third modification example of the present embodiment.

DETAILED DESCRIPTION

An ultrasound diagnosis apparatus according to an embodiment includes an obtaining unit, an image generating unit, and a controlling unit. The obtaining unit obtains setting information in which a plurality of types of ultrasound image data are set as display-purpose image data and in which a percentage of a time period to display the display-purpose image data is set for each of the plurality of types. The image generating unit generates, along a time series, each of the plurality of types of ultrasound image data set in the setting information. The controlling unit exercises control so that the plurality of types of ultrasound image data generated by the image generating unit are stored into a storage unit and exercises control so that the display-purpose image data is displayed on a display unit according to the percentage set in the setting information for each of the types.

Exemplary embodiments of an ultrasound diagnosis apparatus will be explained in detail below, with reference to the accompanying drawings.

Figure 1:
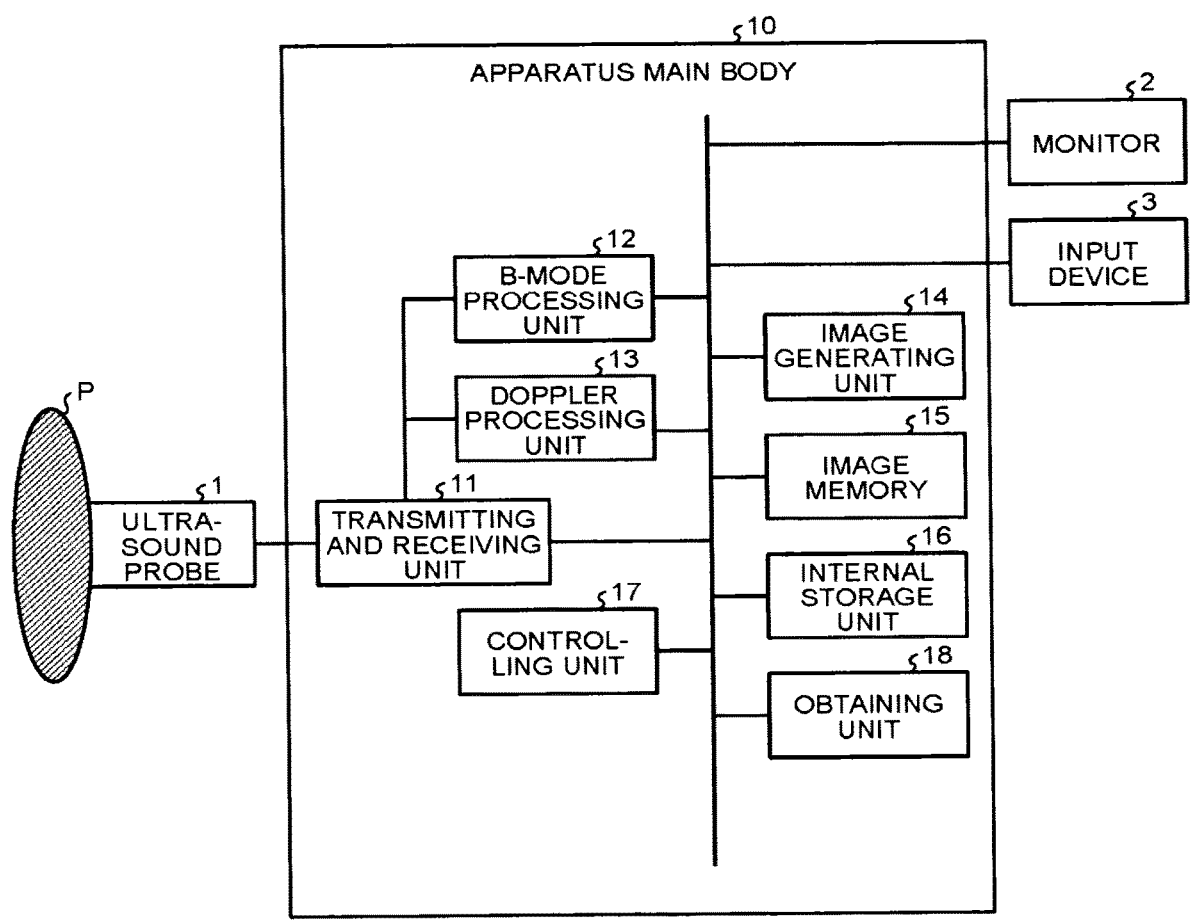
FIG. 1 is a block diagram of an exemplary configuration of an ultrasound diagnosis apparatus according to an embodiment.

First, a configuration of an ultrasound diagnosis apparatus according to an exemplary embodiment will be explained. FIG. 1 is a block diagram of an exemplary configuration of the ultrasound diagnosis apparatus according to the present embodiment. As shown in FIG. 1, the ultrasound diagnosis apparatus according to the present embodiment includes an ultrasound probe 1, a monitor 2, an input device 3, and an apparatus main body 10.

The ultrasound probe 1 includes a plurality of piezoelectric transducer elements, which generate an ultrasound wave based on a drive signal supplied from a transmitting and receiving unit 11 included in the apparatus main body 10 (explained later). Further, the ultrasound probe 1 receives a reflected wave from a subject P and converts the received reflected wave into an electric signal. Further, the ultrasound probe 1 includes matching layers included in the piezoelectric transducer elements, as well as a backing member that prevents ultrasound waves from propagating rearward from the piezoelectric transducer elements. The ultrasound probe 1 is detachably connected to the apparatus main body 10.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving members with respect to the ultrasound wave transmission direction.

The present embodiment is applicable to a situation where the ultrasound probe 1 is a one-dimensional (1D) array probe configured to scan the subject F two-dimensionally and to a situation where the ultrasound probe 1 is a mechanical four-dimensional (4D) probe or a two-dimensional (2D) array probe configured to scan the subject P three-dimensionally. Like the 1D array probe, the mechanical 4D probe is able to perform a two-dimensional scan by employing a plurality of piezoelectric transducer elements arranged in a row and is also able to perform a three-dimensional scan by causing a plurality of piezoelectric transducer elements to swing at a predetermined angle (a swinging angle). In contrast, the 2D array probe is able to perform a three-dimensional scan by employing a plurality of piezoelectric transducer elements arranged in a matrix formation and is also able to perform a two-dimensional scan by transmitting ultrasound waves in a converged manner.

The input device 3 includes a mouse, a keyboard, a button, a panel switch, a touch command screen, a foot switch, a trackball, a joystick, and the like. The input device 3 receives various types of setting requests from an operator of the ultrasound diagnosis apparatus and transfers the received various types of setting requests to the apparatus main body 10. Setting information received from the operator by the input device 3 according to the present embodiment will be explained in detail later.

The monitor 2 displays a Graphical User Interface (GUI) used by the operator of the ultrasound diagnosis apparatus to input the various types of setting requests through the input device 3 and displays ultrasound image data and the like generated by the apparatus main body 10.

The apparatus main body 10 is an apparatus that generates ultrasound image data based on the reflected-wave signal received by the ultrasound probe 1. The apparatus main body 10 shown in FIG. 1 is an apparatus configured to be able to generate two-dimensional ultrasound image data, based on a two-dimensional reflected-wave signal and configured to be able to generate three-dimensional ultrasound image data, based on a three-dimensional reflected-wave signal. It should be noted, however, that the present embodiment is also applicable to a situation where the apparatus main body 10 is an apparatus exclusively for two-dimensional data.

As shown in FIG. 1, the apparatus main body 10 includes the transmitting and receiving unit 11, a B-mode processing unit 12, a Doppler processing unit 13, an image generating unit 14, an image memory 15, an internal storage unit 16, a controlling unit 17, and an obtaining unit 18.

The transmitting and receiving unit 11 controls the ultrasound wave transmissions and receptions performed by the ultrasound probe 1, on the basis of instructions from the controlling unit 17 (explained later). The transmitting and receiving unit 11 includes a pulse generator, a transmission delaying unit, a pulser, and the like and supplies the drive signal to the ultrasound probe 1. The pulse generator repeatedly generates a rate pulse for forming a transmission ultrasound wave at a predetermined rate frequency. Further, the transmission delaying unit applies a delay period that is required to focus the ultrasound wave generated by the ultrasound probe 1 into the form of a beam and to determine transmission directionality and that corresponds to each of the piezoelectric transducer elements, to each of the rate pulses generated by the pulse generator. Further, the pulser applies a drive signal (a drive pulse) to the ultrasound probe 1 with timing based on the rate pulses. In other words, the transmission delaying unit arbitrarily adjusts the transmission directions of the ultrasound waves transmitted from the piezoelectric transducer element surfaces, by varying the delay periods applied to the rate pulses.

The transmitting and receiving unit 11 has a function to be able to instantly change the transmission frequency, the transmission drive voltage, and the like, for the purpose of executing a predetermined scanning sequence based on an instruction from the controlling unit 17 (explained later). In particular, the configuration to change the transmission drive voltage is realized by using a linear-amplifier-type transmitting circuit of which the value can be instantly switched or by using a mechanism configured to electrically switch between a plurality of power source units.

The transmitting and receiving unit 11 includes a pre-amplifier, an Analog/Digital (A/D) converter, a reception delaying unit, an adder, and the like and generates reflected-wave data by performing various types of processes on the reflected-wave signal received by the ultrasound probe 1. The pre-amplifier amplifies the reflected-wave signal for each of channels. The A/D converter applies an A/D conversion to the amplified reflected-wave signal. The reception delaying unit applies a delay period required to determine reception directionality to the result of the A/D conversion. The adder performs an adding process on the reflected-wave signals processed by the reception delaying unit so as to generate the reflected-wave data. As a result of the adding process performed by the adder, reflected components from the direction corresponding to the reception directionality of the reflected-wave signals are emphasized. A comprehensive beam used in an ultrasound wave transmission/reception is thus formed according to the reception directionality and the transmission directionality.

When a two-dimensional scan is performed on the subject P, the transmitting and receiving unit 11 causes the ultrasound probe 1 to transmit two-dimensional ultrasound beams. The transmitting and receiving unit 11 then generates two-dimensional reflected-wave data from the two-dimensional reflected-wave signals received by the ultrasound probe 1. In contrast, when a three-dimensional scan is performed on the subject P, the transmitting and receiving unit 11 causes the ultrasound probe 1 to transmit three-dimensional ultrasound beams. The transmitting and receiving unit 11 then generates three-dimensional reflected-wave data from the three-dimensional reflected-wave signals received by the ultrasound probe 1.

In this situation, output signals from the transmitting and receiving unit 11 can be in a form selected from various forms. For example, the output signals may be in the form of signals called Radio Frequency (RF) signals that contain phase information or may be in the form of amplitude information obtained after an envelope detection process.

The B-mode processing unit 12 and the Doppler processing unit 13 are signal processing units configured to perform various types of signal processing processes on the reflected-wave signals received by the ultrasound probe 1 (i.e., the reflected-wave data generated by the transmitting and receiving unit 11 from the reflected-wave signals). The B-mode processing unit 12 receives the reflected-wave data from the transmitting and receiving unit 11 and generates data (B-mode data) in which the strength of each signal is expressed by a degree of brightness, by performing a logarithmic amplification, an envelope detection process, and the like on the received reflected-wave data. Further, the Doppler processing unit 13 performs a frequency analysis so as to obtain velocity information from the reflected-wave data received from the transmitting and receiving unit 11, and further generates data (Doppler data) obtained by extracting moving member information such as a velocity, a dispersion, a power, and the like under the influence of the Doppler effect for a plurality of points. In this situation, the moving member may be, for example, bloodstream, a tissue such as the cardiac wall, or a contrast agent.

The B-mode processing unit 12 and the Doppler processing unit 13 shown in FIG. 1 are able to process both two-dimensional reflected-wave data and three-dimensional reflected-wave data. In other words, the B-mode processing unit 12 is able to generate two-dimensional B-mode data from two-dimensional reflected-wave data and to generate three-dimensional B-mode data from three-dimensional reflected-wave data. The Doppler processing unit 13 is able to generate two-dimensional Doppler data from two-dimensional reflected-wave data and to generate three-dimensional Doppler data from three-dimensional reflected-wave data.

The image generating unit 14 generates ultrasound image data from the data generated by the B-mode processing unit 12 and the Doppler processing unit 13. In other words, from the two-dimensional B-mode data generated by the B-mode processing unit 12, the image generating unit 14 generates two-dimensional B-mode image data in which the strength of the reflected wave is expressed by a degree of brightness. Further, from the two-dimensional Doppler data generated by the Doppler processing unit 13, the image generating unit 14 generates two-dimensional Doppler image data expressing moving member information. The two-dimensional Doppler image data may be velocity image data, dispersion image data, power image data, or image data combining any of these types of image data.

Further, the image generating unit 14 is also able to generate M-mode image data from time-series data of the B-mode data obtained on one scanning line and generated by the B-mode processing unit 12. Further, from the Doppler data generated by the Doppler processing unit 13, the image generating unit 14 is also able to generate a Doppler waveform in which velocity information of bloodstream or a tissue in a sample volume set by the operator is plotted along a time series.

In this situation, generally speaking, the image generating unit 14 converts (by performing a scan convert process) a scanning line signal sequence from an ultrasound scan into a scanning line signal sequence in a video format used by, for example, television and generates display-purpose ultrasound image data. More specifically, the image generating unit 14 generates the display-purpose ultrasound image data by performing a coordinate transformation process compliant with the ultrasound scanning mode used by the ultrasound probe 1. Further, as various types of image processing processes other than the scan convert process, the image generating unit 14 performs, for example, an image processing process (a smoothing process) to re-generate a brightness-average image, while using a plurality of image frames obtained after the scan convert process is performed, or an image processing process (an edge enhancement process) using a differential filter within images. Further, the image generating unit 14 synthesizes text information of various parameters, scale graduations, body marks, and the like with the ultrasound image data.

In other words, the B-mode data and the Doppler data are the ultrasound image data before the scan convert process is performed. The data generated by the image generating unit 14 is the display-purpose ultrasound image data obtained after the scan convert process is performed. The B-mode data and the Doppler data may also be referred to as raw data. The image generating unit 14 generates "two-dimensional B-mode image data or two-dimensional Doppler image data", which is display-purpose two-dimensional ultrasound image data, from "two-dimensional B-mode data or two-dimensional Doppler data", which is the two-dimensional ultrasound image data before the scan convert process is performed.

Further, the image generating unit 14 generates three-dimensional B-mode image data by performing a coordinate transformation process on the three-dimensional B-mode data generated by the B-mode processing unit 12. Further, the image generating unit 14 generates three-dimensional Doppler image data by performing a coordinate transformation process on the three-dimensional Doppler data generated by the Doppler processing unit 13. The image generating unit 14 generates "the three-dimensional B-mode image data or the three-dimensional Doppler image data" as "three-dimensional ultrasound image data (volume data)".

Further, the image generating unit 14 performs a rendering process on the volume data so as to generate various types of two-dimensional image data used for displaying the volume data on the monitor 2. An example of the rendering process performed by the image generating unit 14 is a process to generate Multi Planar Reconstruction (MPR) image data from the volume data by implementing an MPR method. Another example of the rendering process performed by the image generating unit 14 is a volume rendering (VR) process to generate two-dimensional image data that reflects three-dimensional information.

In this situation, generally speaking, the Doppler image data generated from the Doppler data (bloodstream Doppler data) obtained by extracting moving member information of bloodstream for a plurality of points can roughly divided into color Doppler image data obtained by implementing a color Doppler method and power image data obtained by implementing a power Doppler method. When implementing the color Doppler method, the image generating unit 14 generates color Doppler image data in which hues are changed in accordance with the direction of the bloodstream and the level of velocity of the bloodstream. Alternatively, when implementing the color Doppler method, the image generating unit 14 may generate color Doppler image data used for realizing a velocity-dispersion display in which velocity information is combined with dispersion information. In contrast, when implementing the power Doppler method, the image generating unit 14 generates power image data in which, for example, hues, lightness or chromes of a red-color system is changed in accordance with a power value that expresses the intensity of a Doppler signal.

Further, when implementing a tissue Doppler method, the image generating unit 14 generates tissue Doppler image data from Doppler data (tissue Doppler data) obtained by extracting moving member information of a tissue for a plurality of points.

As explained above, when operating in the B-mode, the image generating unit 14 generates the B-mode image data from the B-mode data. Further, when operating in the color Doppler mode, the image generating unit 14 generates the color Doppler image data from the bloodstream Doppler data. When operating in the power Doppler mode, the image generating unit 14 generates the power Doppler image data from the bloodstream Doppler data. Further, when operating in the tissue Doppler mode, the image generating unit 14 generates the tissue Doppler image data from the tissue Doppler data.

In this situation, the Doppler image data is usually superimposed on the B-mode image data. When performing a two-dimensional scan or a three-dimensional scan, the transmitting and receiving unit 11 performs, in parallel to one another, a B-mode scan in which an ultrasound beam is transmitted and received one time by using one scanning line and a Doppler-mode scan in which an ultrasound beam is transmitted and received a plurality of times by using one scanning line. The Doppler processing unit 13 generates the Doppler data by performing a Moving Target Indicator (MTI) filtering process, an autocorrelation calculating process, and a velocity/dispersion/power estimating process on a plurality of pieces of reflected-wave data from mutually the same scanning line.

Alternatively, according to another method, for the purpose of improving the frame rate or the volume rate, a Doppler-mode scan may be performed by transmitting and receiving an ultrasound beam one time by using one scanning line, like in the B-mode scan. When implementing this method, the Doppler processing unit 13 generates the Doppler data by performing an MTI filtering process, an autocorrelation calculating process, and a velocity/dispersion/power estimating process along either the frame direction or the volume direction, on a plurality of pieces of reflected-wave data in mutually the same position of mutually-different frames or mutually-different volumes.

Further, other than the ultrasound image data described above, the image generating unit 14 is capable of generating various types (modes) of ultrasound image data. For example, when operating in an elastography mode to realize elastography imaging, the image generating unit 14 generates image data (elasticity image data) in which hardness (elastic modulus) of a tissue is expressed in an image, from the reflected-wave data (the reflected-wave signals) on which a signal processing process has been performed by the Doppler processing unit 13. For example, in the elastography mode, the operator applies pressure to a tissue of the subject's body by using the surfaces of the transducer elements of the ultrasound probe 1 performing the ultrasound wave transmissions/receptions and subsequently releases the pressure. As a result, the tissue changes the shape thereof, and a movement is thus created with the tissue. Information related to the movement of the tissue is exhibited as a phase shift in the reflected-wave signals (the reflected-wave data).

When operating in the elastography mode, for example, the Doppler processing unit 13 calculates velocity information on the basis of the phase shift in the reflected-wave data, and further measures a displacement, which is calculated by time-integrating the velocity information. Further, by calculating a spatial differential of the displacement, the Doppler processing unit 13 calculates a strain. Examples of methods for measuring the displacement include the "autocorrelation method", the "cross-correlation method", a "complex autocorrelation method", and a "zero phase method". The harder a tissue in the subject's body is, the lower is the tendency for the tissue to change the shape thereof. Consequently, the strain value of a harder tissue in the subject's body is smaller, whereas the strain value of a softer tissue in the subject's body is larger. In other words, the strain value is a value that indicates the hardness (elastic modulus) of the tissue. The image generating unit 14 generates elasticity image data in which color tones are changed in accordance with levels of strain values at a plurality of points, the strain values having been calculated by the Doppler processing unit 13.

In the elastography mode, instead of the method by which the shape of a tissue is changed by applying and releasing pressure using the ultrasound probe 1, another method may be used by which the shape of a tissue is changed by a "push pulse" having a high sound pressure that is transmitted from the ultrasound probe 1 so that a transversal wave called a shear wave that propagates through the tissue is formed and so that elastic modulus of the tissue is further evaluated on the basis of the propagating speed of the shear wave or the like. Further, in the elastography mode, instead of the method by which a shear wave is formed and the method by which pressure is manually applied to and released from a tissue, yet another method may be used by which elastic modulus is calculated by detecting changes in the shape of a tissue caused by, for example, the pulsation or a movement of the diaphragm. Alternatively, elasticity image data may be generated from the reflected-wave data (the reflected-wave signals) on which a signal processing process has been performed by the B-mode processing unit 12. For example, it is also possible to generate elasticity image data by performing a speckle tracking process while using a plurality of pieces of B-mode image data (or B-mode data) generated along a time series and calculating displacements and strains at a plurality of points, on the basis of results obtained by tracking a plurality of tracked points.

Examples of the ultrasound image data generated from the reflected-wave data (the reflected-wave signals) on which a signal processing process has been performed by the B-mode processing unit 12 include calcification enhanced image data, statistical analysis image data, harmonic component image data, in addition to the B-mode image data (and the elasticity image data).

The calcification enhanced image data is ultrasound image data generated in a calcification enhanced mode. In the following sections, the calcification enhanced mode will simply be referred to as the "enhanced mode". In the enhanced mode, an image processing process is performed for the purpose of improving visibility of microcalcification. In the enhanced mode, images of mimicking patches that look like microcalcification are eliminated from the B-mode image data, by performing a statistical analysis of the signal amplitude. Further, in the enhanced mode, on the basis of the characteristic that microcalcification is isolated on high levels of echo signals, continuous structures such as structures of mammary glands are eliminated from the B-mode image data so that microstructures corresponding to microcalcification are eventually extracted.

Further, in the enhanced mode, image data in which the extracted microstructures are expressed in white is generated. Further, in the enhanced mode, superimposed image data obtained by superimposing together the "image data in which the microstructures are rendered in white" and "image data in which the B-mode image data from which the microstructures have been extracted is rendered in a blue-color system" is generated as calcification enhanced image data. The microstructures (the microcalcification) is extracted as a result of, for example, a filtering process performed by the B-mode processing unit 12 or the image generating unit 14 on the B-mode image data (or the B-mode data).

The statistical analysis image data is ultrasound image data generated in the "Acoustic Structure Quantification (ASQ) mode". In the ASQ mode, an image processing process is performed to make a tissue characterization diagnosis such as, for example, a degree of tissue fibrillization. In the ASQ mode, a degree of deviation (a dispersion value) from a Rayleigh distribution of a signal amplitude distribution of the reflected-wave data (the reflected-wave signals) is calculated, so that data obtained by expressing the calculated dispersion value in an image is generated as the statistical analysis image data. The dispersion value compared to the Rayleigh distribution may be extracted as a result of, for example, a statistical similarity filtering process performed by the B-mode processing unit 12 or the image generating unit 14 on the B-mode image data (or the B-mode data).

In some situations, the calcification enhanced image data and the statistical analysis image data may be generated from, for example, reflected-wave data corresponding to a plurality of frames.

The harmonic component image data is ultrasound image data generated in a mode to perform a Contrast Harmonic Imaging (CHI) process or a Tissue Harmonic Imaging (THI) process. The B-mode processing unit 12 shown in FIG. 1 is able to change the frequency bandwidth to be realized in a picture, by changing detected frequencies. More specifically, the B-mode processing unit 12 is able to separate B-mode data of harmonic components, which are non-linear signals, from the B-mode data.

For example, when operating in the CHI mode, the B-mode processing unit 12 separates B-mode data of a second harmonic component from the B-mode data corresponding to one frame obtained by scanning the subject P into whom an ultrasound contrast agent has been injected. Further, the image generating unit 14 generates harmonic component image data (contrast enhanced image data) in which the ultrasound contrast agent is imaged with high sensitivity, from the B-mode data of the second harmonic component.

Further, when operating in the THI mode, for example, the B-mode processing unit 12 separates B-mode data of the second harmonic component from the B-mode data corresponding to one frame obtained by scanning the subject P. Further, the image generating unit 14 generates harmonic component image data in which side-lobe effects are reduced, from the B-mode data of the second harmonic component.

In this situation, the B-mode processing unit 12 extracts the harmonic components from the B-mode data corresponding to the one frame by performing a filtering process. Alternatively, the harmonic components may be extracted as a result of a process performed by the B-mode processing unit 12 while using the reflected-wave data generated from reflected-wave signals in a plurality of ultrasound wave transmissions performed by the ultrasound probe 1 a plurality of times.

For example, when implementing a pulse inversion method, which is a type of phase modulating method, the ultrasound probe 1 transmits ultrasound waves twice of which the amplitudes are the same as each other and of which the phases are different from each other, under the control of the transmitting and receiving unit 11. More specifically, at the second time, the ultrasound probe 1 transmits an ultrasound wave of which the phase of the transmission waveform is different by 180 degrees from that of the transmission waveform transmitted at the first time. As a result, the transmitting and receiving unit 11 generates two pieces of reflected-wave data. The B-mode processing unit 12 is thus able to obtain "data in which the fundamental harmonic component is suppressed and in which the second harmonic component is doubled", by adding together the two pieces of reflected-wave data received from the transmitting and receiving unit 11.

As another example, when implementing a method in which a phase modulating method is combined with an amplitude modulating method, the ultrasound probe 1 transmits ultrasound waves three times of which the ratio among the amplitudes satisfies "1:2:1", of which the phases in the first transmission and the third transmission are the same as each other, and of which the phase in the first transmission and the second transmission are different from each other by 180 degrees, under the control of the transmitting and receiving unit 11. As a result, the transmitting and receiving unit 11 generates three pieces of reflected-wave data. The B-mode processing unit 12 is thus able to obtain "data in which the fundamental harmonic component is suppressed and in which the second harmonic component is doubled", by adding together the three pieces of reflected-wave data received from the transmitting and receiving unit 11.

Figure 2:
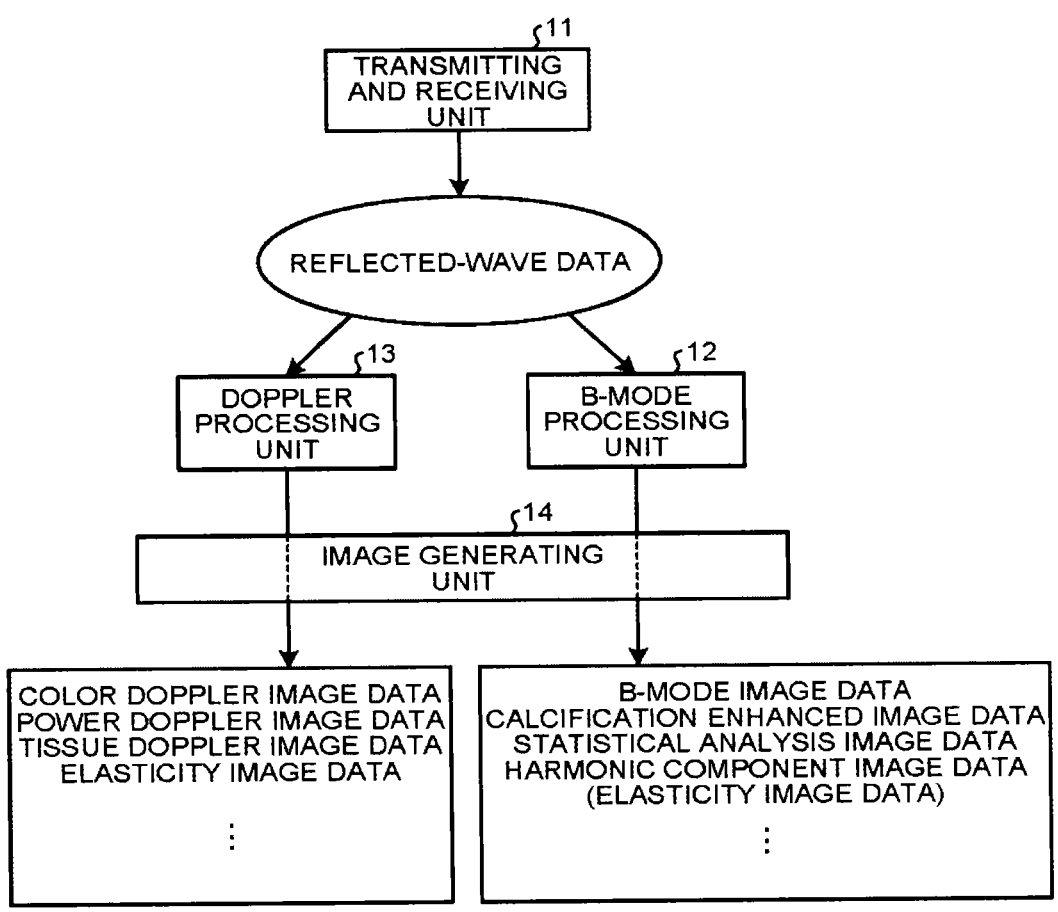
FIG. 2 is a drawing that illustrates examples of types of ultrasound image data generated by the ultrasound diagnosis apparatus according to the present embodiment.

As explained above, the ultrasound diagnosis apparatus according to the present embodiment is able to generate ultrasound image data having various characteristics, by changing the ultrasound wave transmitting/receiving method and the reception signal processing method according to each of the modes. The description above is summarized in FIG. 2. FIG. 2 is a drawing that illustrates examples of types of ultrasound image data generated by the ultrasound diagnosis apparatus according to the present embodiment.

As illustrated in FIG. 2, the color Doppler image data, the power Doppler image data, the tissue Doppler image data, the elasticity image data, and the like are each ultrasound image data generated by the image generating unit 14 on the basis of the data resulting from a signal processing process performed by the Doppler processing unit 13 on the reflected-wave data generated by the transmitting and receiving unit 11. Although not illustrated in FIG. 2, other examples of the ultrasound image data generated by the image generating unit 14 on the basis of the data resulting from a signal processing process performed by the Doppler processing unit 13 on the reflected-wave data generated by the transmitting and receiving unit 11 include Doppler waveform data obtained by plotting, along a time series, bloodstream velocity information in a range set by the operator in the B-mode image data or the color Doppler image data. For example, when operating in a Pulsed Wave (PW) mode in which a Doppler waveform is acquired by implementing a PW Doppler method, the image generating unit 14 generates Doppler waveform data indicating bloodstream velocity information within a sampling gate that is set by the operator in a specific site of a blood vessel rendered in the B-mode image data. In another example, when operating in a Continuous Wave (CW) mode in which a Doppler waveform is acquired by implementing a CW Doppler method, the image generating unit 14 generates Doppler waveform data indicating all of the bloodstream velocity information on a sampling line that is set by the operator on scanning lines that pass through a blood vessel rendered in the B-mode image data. Further, as illustrated in FIG. 2, the B-mode image data, the calcification enhanced image data, the statistical analysis image data, the harmonic component image data (and the elasticity image data) are each ultrasound image data generated by the image generating unit 14 on the basis of the data resulting from a signal processing process performed by the B-mode processing unit 12 on the reflected-wave data generated by the transmitting and receiving unit 11.

As explained above, the plurality of types of ultrasound image data displayed by the ultrasound diagnosis apparatus according to the present embodiment are each a type of ultrasound image data which the image generating unit 14 is capable of generating from the data obtained by performing one of a plurality of feature extraction processes or by performing a process combining together two or more feature extraction processes selected out of the plurality of feature extraction processes, on the reflected-wave signals (the reflected-wave data). Examples of the plurality of feature extraction processes include a "signal amplitude feature extraction process" such as an envelope detection process, an "intensity feature extraction process" performed for the purpose of assigning brightness levels in the B-mode data, and a "frequency feature extraction process" performed for the purpose of detecting changes in the frequency due to the Doppler effect. Further, other examples of the plurality of feature extraction processes include a "spatial correlation feature extraction process" performed for the purpose of processing a cross-correlation within a frame and a "temporal correlation feature extraction process" performed for the purpose of processing a cross-correlation between frames.

In this situation, the ultrasound image data (e.g., the B-mode image data, the calcification enhanced image data, the statistical analysis image data, the harmonic component image data) generated by the image generating unit 14 from the data resulting from a signal processing process performed by the B-mode processing unit 12 is ultrasound image data generated by the image generating unit 14 from the data resulting from a signal processing process including an intensity feature extraction process.

Returning to the description of FIG. 1, the image memory 15 is a memory for storing therein the display-purpose image data generated by the image generating unit 14. Further, the image memory 15 is also able to store therein the data generated by the B-mode processing unit 12 and the Doppler processing unit 13. After a diagnosis process, for example, the operator is able to invoke the B-mode data or the Doppler data stored in the image memory 15. The invoked data serves as the display-purpose ultrasound image data via the image generating unit 14.

The internal storage unit 16 stores therein various types of data such as a control computer program (hereinafter, a "control program") to realize the ultrasound wave transmissions and receptions, image processing, and display processing, as well as diagnosis information (e.g., patients' IDs, medical doctors' observations), diagnosis protocols, and various types of body marks. Further, the internal storage unit 16 may be used, as necessary, for storing therein any of the image data stored in the image memory 15. Further, it is possible to transfer the data stored in the internal storage unit 16 to external apparatuses via an interface (not shown). Examples of the external apparatuses include a personal computer (PC) used by a medical doctor who performs an image diagnosis process, a storage medium such as a Compact Disk (CD) or a Digital Versatile Disc (DVD), a printer, and the like.

The reflected-wave data generated by the transmitting and receiving unit 11 is temporarily stored into a frame buffer (not shown). Also, the present embodiment may be configured so that the reflected-wave data generated by the transmitting and receiving unit 11 is stored into the image memory 15 or the internal storage unit 16 in a non-transitory manner.

The controlling unit 17 controls the entire processes performed by the ultrasound diagnosis apparatus. More specifically, based on the various types of setting requests input by the operator via the input device 3 and various types of control programs and various types of data read from the internal storage unit 16, the controlling unit 17 controls processes performed by the transmitting and receiving unit 11, the B-mode processing unit 12, the Doppler processing unit 13, and the image generating unit 14. Further, the controlling unit 17 exercises control so that the monitor 2 displays the display-purpose ultrasound image data stored in the image memory 15 and the internal storage unit 16. Further, the controlling unit 17 exercises control so that the display-purpose ultrasound image data generated by the image generating unit 14 is stored into the internal storage unit 16 or the like.

The obtaining unit 18 obtains the setting information (explained later) from the input device 3 or an interface (not shown). For example, the setting information explained later is information obtained by the obtaining unit 18 as a result of the information being input through the input device 3 by the operator who performs an ultrasound examination by using the ultrasound diagnosis apparatus. Alternatively, the setting information explained below may be, for example, information obtained by the obtaining unit 18 from an external apparatus via an interface as information written in a medical examination request made by a medical doctor who requests an ultrasound examination.

An overall configuration of the ultrasound diagnosis apparatus according to the present embodiment has thus been explained. The ultrasound diagnosis apparatus according to the first embodiment configured as described above acquires, during an ultrasound examination, a plurality of types of ultrasound image data by using any of the various types of modes described above.

During a conventional ultrasound examination, generally speaking, image data in one of a plurality of modes (e.g., the B-mode) is taken at first. Alternatively, during a conventional ultrasound examination, image taking processes in two modes (e.g., the B-mode and the Doppler mode) may be performed at the same time, so that pieces of image data in the two modes are displayed side by side or displayed in a superimposed manner. Further, when making an examination observation while using the image in the mode used at first or when performing an examination routine that is determined in advance, the operator manually switches the image taking mode to another mode.

In the conventional ultrasound examination described above, however, because the switching between the plurality of image taking modes is manually performed, a large burden is imposed on the operator. For example, because the switching between the modes is manually performed, there is a possibility that an image taking process in a mode that is optimal for making an image diagnosis of a certain disease may be missing from the procedure.

To cope with this situation, to collectively and easily obtain the information required to make a diagnosis from an ultrasound examination, the ultrasound diagnosis apparatus according to the present embodiment is configured so that the obtaining unit 18 obtains the setting information explained below and notifies the controlling unit 17 of the obtained setting information and so that the controlling unit 17 controls the image generating unit 14 and the like while using the notified setting information.

More specifically, the setting information obtained by the obtaining unit 18 is information in which a plurality of pieces of ultrasound image data are set as display-purpose image data. Even more specifically, the setting information obtained by the obtaining unit 18 is information in which a plurality of types of ultrasound image data are set as the display-purpose image data. In this situation, the plurality of types of ultrasound image data set as the display-purpose image data include a plurality of types of ultrasound image data that are generatable from reflected-wave signals (reflected-wave data) on which signal processing processes of mutually the same type have been performed. The signal processing processes of mutually the same type are signal processing processes including the intensity feature extraction process.

In other words, the plurality of types of ultrasound image data that are set as the display-purpose image data include a plurality of types of ultrasound image data (e.g., the B-mode image data and the calcification enhanced image data) that are generatable from the reflected-wave signals (the reflected-wave data) on which the B-mode processing process has been performed. In this situation, the plurality of types of ultrasound image data set as the display-purpose image data may be represented only by a plurality of types of ultrasound image data that are generatable from data on which the B-mode processing process has been performed. The display-purpose image data is a plurality of types of ultrasound image data that are judged by the operator or a medical doctor to be essential in making an image diagnosis for the subject P. Further, the plurality of types of ultrasound image data set as the display-purpose image data may be two-dimensional ultrasound image data, two-dimensional image data based on three-dimensional ultrasound image data, or data in which both two-dimensional ultrasound image data and two-dimensional image data based on three-dimensional ultrasound image data are present in a mixed manner.

Further, the setting information obtained by the obtaining unit 18 is information in which a percentage of a time period to display the display-purpose image data is set for each of the types. The setting information is information in which the percentage of time periods to display the plurality of types of ultrasound image data that are set as the display-purpose image data is set.

The controlling unit 17 is notified of the setting information obtained by the obtaining unit 18. Further, under the control of the controlling unit 17 that has received the setting information, the image generating unit 14 generates, along a time series, each of the plurality of types of ultrasound image data set in the setting information. Further, the controlling unit 17 exercises control so that the plurality of types of ultrasound image data generated by the image generating unit 14 are stored into the internal storage unit 16. Further, the controlling unit 17 exercises control so that the plurality of types of ultrasound image data generated by the image generating unit 14 are displayed on the monitor 2 according to the percentage of time periods set in the setting information.

Figures 3, 4:
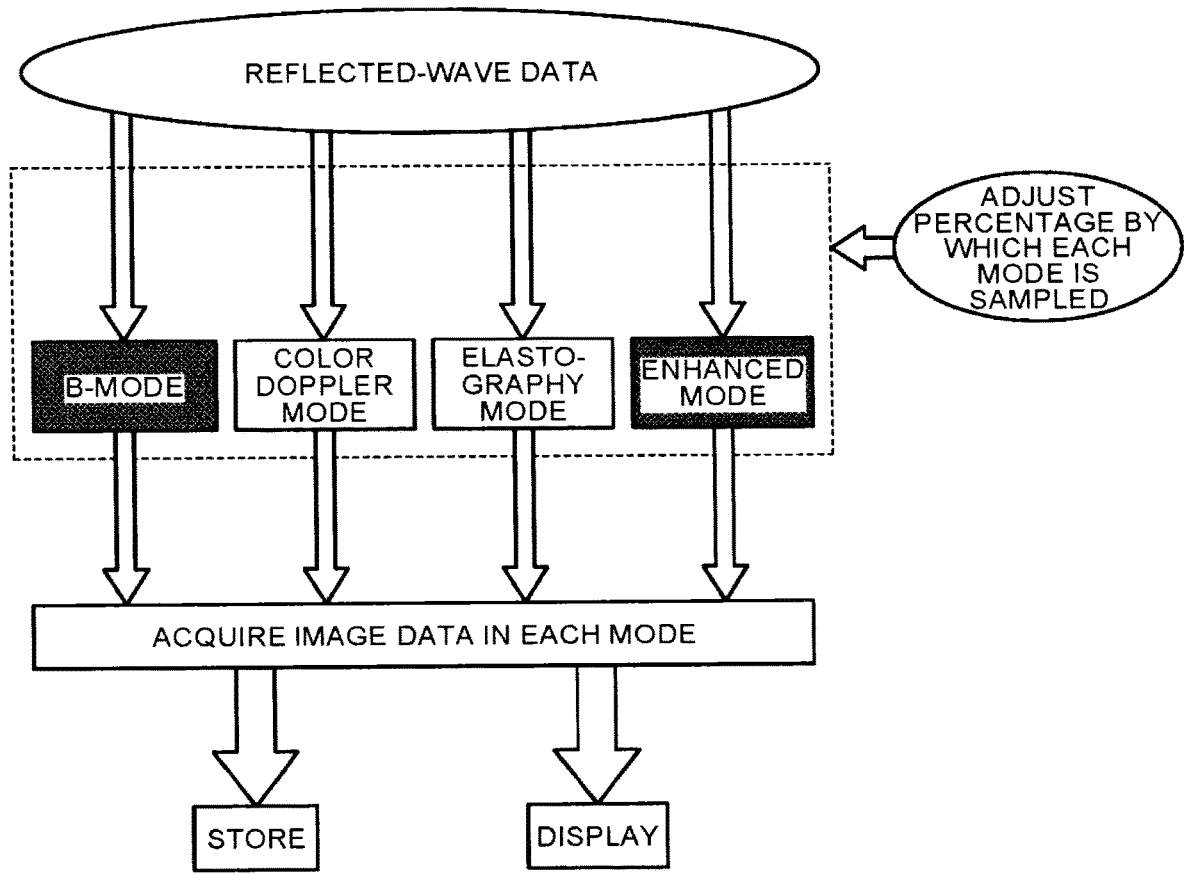
FIG. 3 is a schematic drawing of processes that are performed while using setting information according to the present embodiment.
FIG. 4 is a drawing that illustrates an example of the setting information.

FIG. 3 is a schematic drawing of processes that are performed while using the setting information according to the present embodiment. In the schematic drawing shown in FIG. 3, the operator has made a setting so that pieces of ultrasound image data in the B-mode, the color Doppler mode, the elastography mode, and the enhanced mode are acquired as the display-purpose image data. The image data in the B-mode and the image data in the enhanced mode are each image data using B-mode data. In contrast, the image data in the color Doppler mode and the image data in the elastography mode are each image data using Doppler data.

Further, as shown in FIG. 3, the operator sets the percentage of display time periods described above, so as to adjust the percentage by which each of the modes is sampled. The controlling unit 17 that has received the setting information from the obtaining unit 18 controls the transmitting and receiving unit 11, the B-mode processing unit 12, the Doppler processing unit 13, and the image generating unit 14, so that the ultrasound wave transmitting/receiving method and the signal processing method change in accordance with the mode that is currently set. As a result, as shown in FIG. 3, the controlling unit 17 causes the image data in each of the modes to be acquired and exercises storage control and display control over the acquired image data in each of the modes.

Figure 5A:
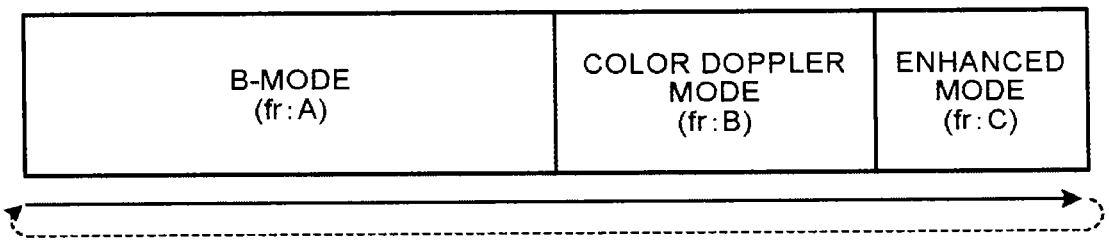
FIG. 5A, FIG. 5B and FIG. 5C are drawings of an example of a display plan based on the setting information illustrated in FIG. 4.
Figure 5B:
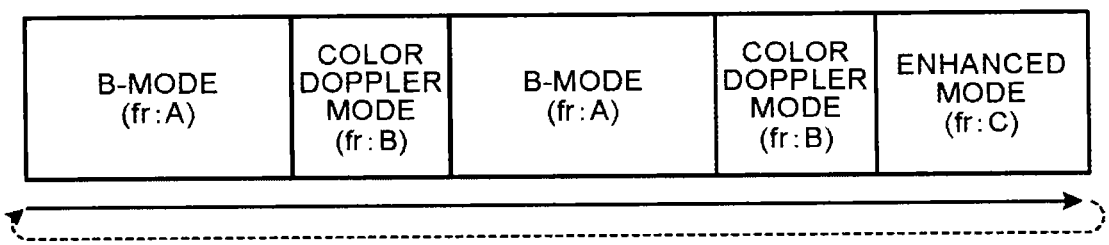
Figure 5C:
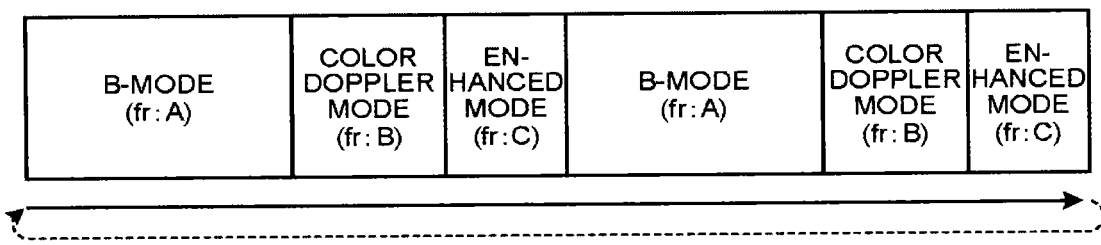

Next, the processes described above will be explained further in detail, by using an example of the setting information shown in FIG. 4. FIG. 4 is a drawing that illustrates an example of the setting information. For example, as shown in FIG. 4, the operator sets three types of ultrasound image data in the B-mode, the color Doppler mode, and the enhanced mode as the display-purpose image data. After that, for example, as shown in FIG. 4, the operator sets percentage values indicating that the percentage to display the B-mode image data is "50%", the percentage to display the color Doppler mode image data is "30%", and the percentage to display the calcification enhanced image data in the enhanced mode is "20%". The obtaining unit 18 obtains the setting information illustrated in FIG. 4 and transmits the setting information to the controlling unit 17. By referring to the received setting information, the controlling unit 17 sets a display plan as illustrated in FIGS. 5A, 5B, and 5C. FIGS. 5A, 5B, and 5C are drawings of examples of display plans based on the setting information illustrated in FIG. 4.

First, the controlling unit 17 sets frequency with which it is possible to acquire data in each of the modes that are set in the setting information, i.e., sets a frame rate ("fr") for each of the modes. For example, the controlling unit 17 sets a frame rate in the B-mode to "fr: A", sets a frame rate in the color Doppler mode to "fr: B", and sets a frame rate in the enhanced mode to "fr: C". Further, the controlling unit 17 sets a unit time period for displaying each of the modes set in the setting information. In the following sections, an example in which the unit time period is set to ten seconds will be explained.

As illustrated in FIG. 5A, for example, the controlling unit 17 sets a display plan indicating that the image data in the B-mode acquired while using "fr: A" is first displayed for "5 seconds", and subsequently, the image data in the color Doppler mode acquired while using "fr: B" is displayed for "3 seconds", and then, the image data in the enhanced mode acquired while using "fr: C" is displayed for "2 seconds". According to this display plan set by the controlling unit 17, it is indicated that, after ten seconds have elapsed since the beginning of the display, the image data in the B-mode acquired while using "fr: A" is displayed anew again (see the arrow with a dotted line in FIG. 5A).

In another example, as illustrated in FIG. 58B, the controlling unit 17 sets a display plan indicating that the process of first displaying for "2.5 seconds" the image data in the B-mode acquired while using "fr: A", followed by displaying for "1.5 seconds" the image data in the color Doppler mode acquired while using "fr: B" is repeated twice, and subsequently, the image data in the enhanced mode acquired while using "fr: C" is displayed for "2 seconds". Like in the example described above, according to this display plan set by the controlling unit 17, it is indicated that, after ten seconds have elapsed since the beginning of the display, the image data in the B-mode acquired while using "fr: A" is displayed anew again (see the arrow with a dotted line in FIG. 5B).

In yet another example, as illustrated in FIG. 5C, the controlling unit 17 sets a display plan indicating that the process of first displaying for "2.5 seconds" the image data in the B-mode acquired while using "fr: A", followed by displaying for "1.5 seconds" the image data in the color Doppler mode acquired while using "fr: B", and subsequently, displaying for "1 second" the image data in the enhanced mode acquired while using "fr: C" is repeated twice. Like in the example described above, according to this display plan set by the controlling unit 17, it is indicated that, after ten seconds nave elapsed since the beginning of the display, the image data in the B-mode acquired while using "fr: A" is displayed anew again (see the arrow with a dotted line in FIG. 5C).

The frame rates, the unit time period, and the display order do not necessarily have to be automatically set by the controlling unit 17 as illustrated in FIGS. 5A, 5B, and 5C. It is acceptable for the operator to set the frame rates, the unit time period, and the display order, together with the setting information. Further, it is also possible for the operator to change the setting information, the frame rates, the unit time period, and the display order, during the data acquiring process.

Figure 6A:
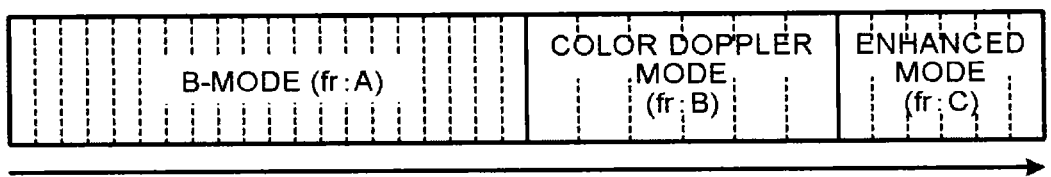
FIG. 6A and FIG. 6B are drawings of an example of image generation control according to the present embodiment.
Figure 6B:
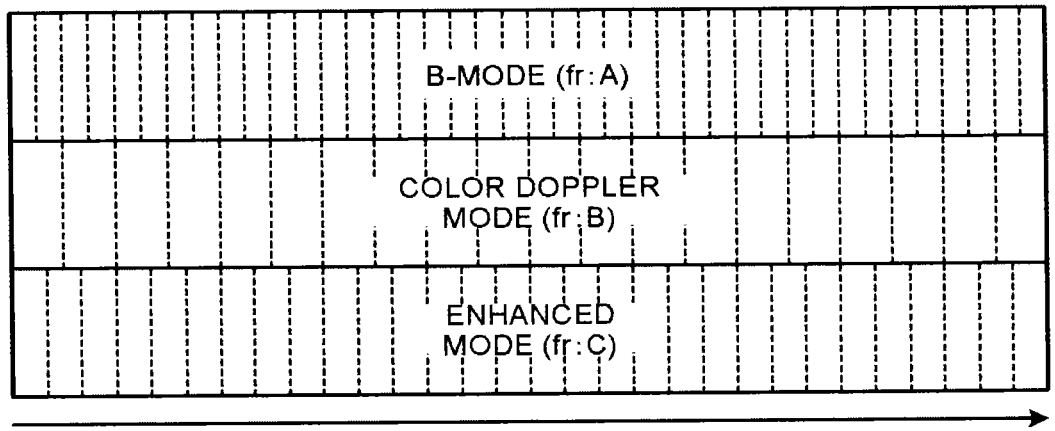

In this situation, under the control of the controlling unit 17, the image generating unit 14 generates, along a time series, each of the plurality of types of ultrasound image data set in the setting information. More specifically, the controlling unit 17 exercises image generation control described below over the image generating unit 14. FIGS. 6A and 6B are drawings of examples of the image generation control according to the present embodiment.

According to a first image generation control method, the image generating unit 14 generates each of the plurality of types of ultrasound image data set in the setting information along a time series and according to the frequency set for the type, while sequentially switching between the types of ultrasound image data to have a generating process performed thereon according to the percentage set in the setting information. For example, under the control of the controlling unit 17 having set the display plan illustrated in FIG. 5A, the image generating unit 14 first generates, as illustrated in FIG. 6A, the image data in the B-mode at "fr: A", subsequently generates the image data in the color Doppler mode at "fr: B", and then, generates the image data in the enhanced mode at "fr: C". In this situation, the image generating unit 14 repeats the process of switching between the generation modes within the unit time period, until an acquisition ending request is received from the operator. Further, under the control of the controlling unit 17, the transmitting and receiving unit 11 exercises ultrasound wave transmission/reception control over the ultrasound probe 1 in accordance with each of the modes.

Alternatively, according to a second image generation control method, the image generating unit 14 generates the plurality of types of ultrasound image data set in the setting information in parallel to one another, along a time series and according to the frequency set for each of the types. For example, under the control of the controlling unit 17 having set the display plans illustrated in FIGS. 5A, 5B, and 5C, the image generating unit 14 performs, as illustrated in FIG. 6B, in parallel to one another, the processes of generating the image data in the B-mode at "fr: A", generating the image data in the color Doppler mode at "fr: B", and generating the image data in the enhanced mode at "fr: C". In this situation, the image generating unit 14 continues to perform the processes of generating the image data in the plurality of modes in parallel to one another, until an acquisition ending request is received from the operator. The second image generation control method is suitable for a situation where it is possible to generate each of the plurality of types of ultrasound image data set in the setting information by performing the same ultrasound wave transmissions/receptions. For example, it is possible to execute the color Doppler mode by implementing the scanning method for the B-mode, as described above. Thus, the image generating unit 14 is able to perform the parallel processes illustrated in FIG. 6B.

In other words, the first image generation control method is a method by which only the frames which the operator requested to have displayed are generated in a real-time manner. In contrast, the second image generation control method is a method by which the frames other than the frames which the operator requested to have displayed are also generated in a real-time manner. Either the operator or the controlling unit 17 determines whether the first image generation control method should be selected or the second image generation control method should be selected, in accordance with the processing capability of the apparatus main body 10. In this situation, if the reflected-wave data is stored in a non-transitory storage medium, the controlling unit 17 may implement a third image generation control method described below.

According to the third image generation control method, the image generating unit 14 generates images by implementing the first image generation control method in a real-time manner. Further, according to the third image generation control method, the image generating unit 14 generates, by performing a post-processing process, various types of ultrasound image data in the frames other than the frames generated in a real-time manner by using the stored reflected-wave data, in such a manner that the quantity of frames eventually generated is equal to the quantity of frames generated by using the second image generation control method. According to the third image generation control method, even if the apparatus main body 10 has a low processing capability, it is possible to eventually generate a group of pieces of ultrasound image data for a diagnosis purpose that is similar to the ultrasound image data generated by implementing the second image generation control method.

Figure 7:
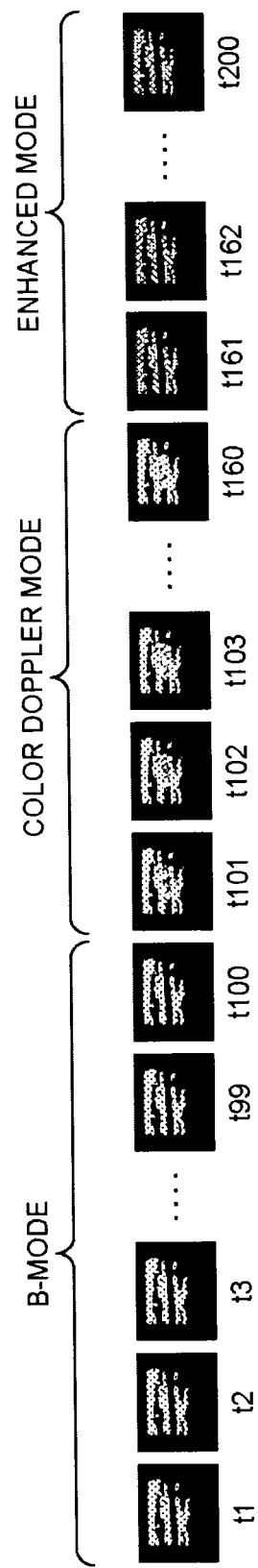
FIG. 7 and FIG. 8 are drawings of an example of storage control according to the present embodiment.
Figure 8:
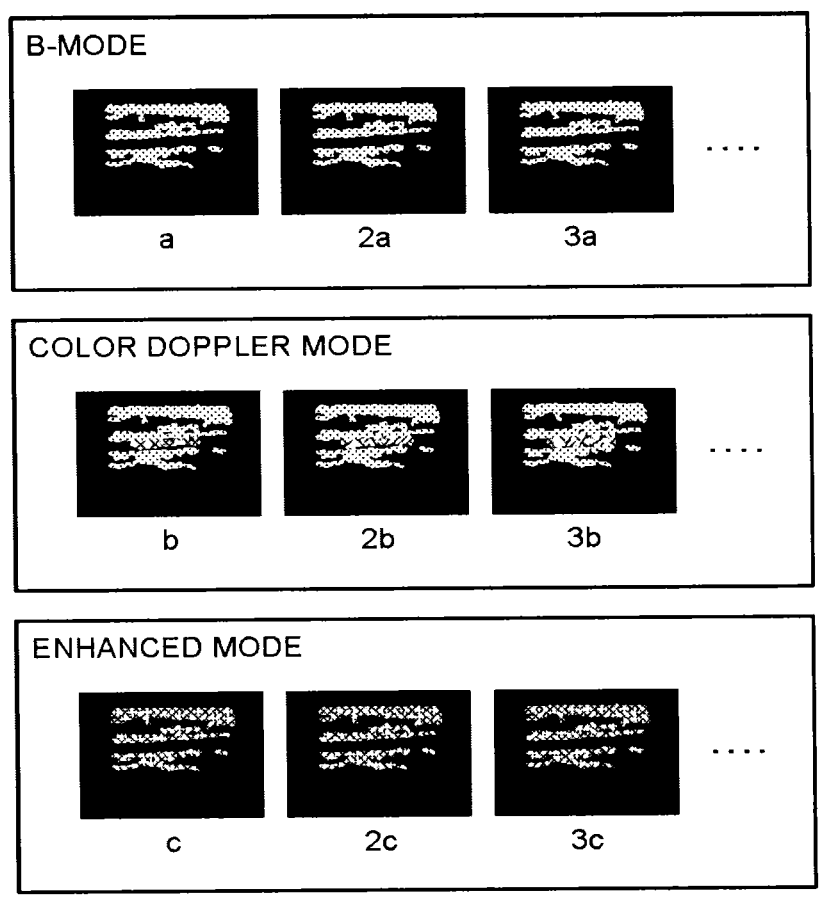

Further, as described above, the controlling unit 17 exercises control so that the plurality of types of ultrasound image data generated by the image generating unit 14 are stored into the internal storage unit 16. More specifically, the controlling unit 17 performs storage control as described below. FIGS. 7 and 8 are drawings of examples of storage control according to the present embodiment.

According to a first storage control method, the controlling unit 17 exercises control so that the plurality of types of ultrasound image data generated by the image generating unit 14 are stored into, for example, mutually the same storage area of the internal storage unit 16 in the order of generation. For example, when images are generated by implementing the first image generation control method illustrated in FIG. 6A, the image generating unit 14 collectively stores the generated pieces of ultrasound image data into mutually the same storage area of the internal storage unit 16 in the order of generation, under the control of the controlling unit 17. In this situation, under the control of the controlling unit 17, the image generating unit 14 collectively stores the generated pieces of ultrasound image data into mutually the same storage area of the internal storage unit 16, while keeping the times at which the pieces of ultrasound image data were generated (hereinafter, "times of generation") in correspondence therewith.

As a result, as illustrated in FIG. 7, the internal storage unit 16 stores therein the image data in the B-mode kept in correspondence with times of generation "t1, t2, t3, . . . t99, and t100", the image data in the color Doppler mode kept in correspondence with times of generation "t101, t102, t103, . . . , and t160", and the image data in the enhanced mode kept in correspondence with times of generation "t161, t162, . . . , and t200". The time period "t200−t1" corresponds to the unit time period described above. Further, the time periods "t2−t1", "t3−t2", and so on each correspond to "a=1/A" because of "fr: A", whereas the time periods "t102−t101", "t103−t102", and so on each correspond to "b=1/B" because of "fr: B", while the time periods "t162−t161", "t163−t162", and so on each correspond to "c=1/C" because of "fr: C".

The first storage control method is also applicable to a situation where a plurality of types of ultrasound image data are generated by implementing the second image generation control method. According to the first storage control method, the ultrasound diagnosis apparatus is able to store therein the group of pieces of image data acquired on the basis of the setting information, without changing the current system configuration.

In another example, according to a second storage control method, for example, the controlling unit 17 exercises control so that, to each of a plurality of storage areas of the internal storage unit 16, a different one of the plurality of types of ultrasound image data generated by the image generating unit 14 is assigned and stored therein in the order of generation. In this situation, under the control of the controlling unit 17, the image generating unit 14 stores the generated pieces of ultrasound image data into the plurality of storage areas of the internal storage unit 16, respectively, so as to be separated according to the types thereof and kept in correspondence with the times of generation thereof.

Figure 9:
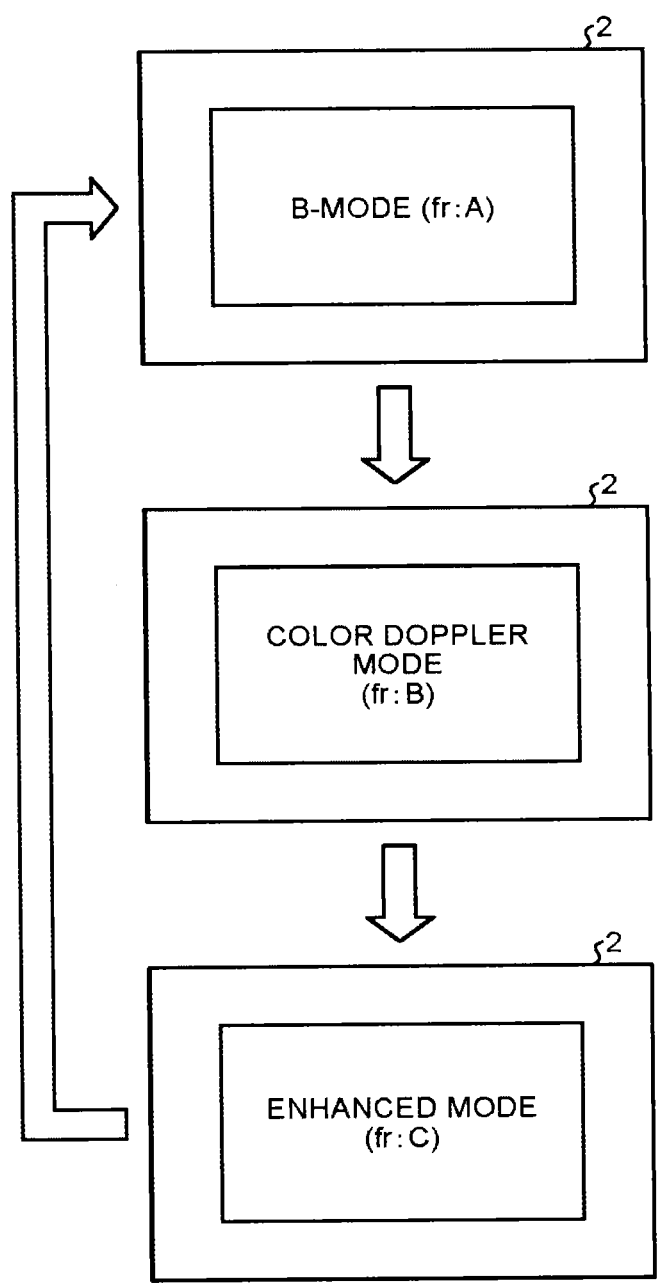
FIG. 9, FIG. 10 and FIG. 11 are drawings of an example of display control according to the present embodiment.

For example, when images are generated by implementing the second image generation control method illustrated in FIG. 6B, under the control of the controlling unit 17, the image generating unit 14 stores, as illustrated in FIG. 8, pieces of B-mode image data that are kept in correspondence with "a, 2a, and 3a" that are elapsed time periods since the acquisition starting time, which serve as the times of generation, into a storage area for the B-mode, in the order of generation. Further, under the control of the controlling unit 17, the image generating unit 14 stores, as illustrated in FIG. 8, pieces of color Doppler image data that are kept in correspondence with elapsed time periods "b, 2b, and 3b", into a storage area for the color Doppler mode, in the order of generation. Further, under the control of the controlling unit 17, the image generating unit 14 stores, as illustrated in FIG. 9, pieces of calcification enhanced image data that are kept in correspondence with elapsed time periods "c, 2c, and 3c", into a storage area for the enhanced mode, in the order of generation.

In this situation, the second storage control method is also applicable to a situation where a plurality of types of ultrasound image data are generated by implementing the first image generation control method. Further, when implementing the third image generation control method, for example, the controlling unit 17 temporarily stores the group of pieces of image data generated by implementing the first image generation control method into the image memory 15 in the order of generation. After that, the controlling unit 17 stores the group of pieces of image data stored in the image memory 15 and the group of pieces of image data generated as a result of the post-processing process into the internal storage unit 16 according to the first storage control method or the second storage control method. According to the second storage control method, it is necessary to change the system configuration of the ultrasound diagnosis apparatus so that the pieces of image data are stored according to the types thereof. However, because the group of pieces of image data acquired on the basis of the setting information is stored according to the types thereof, it is possible to easily read, after the acquisition, each of the different types of image data separately from each other.

The present embodiment may also be configured so that the ultrasound image data acquired according to the setting information is stored into a storage unit other than the internal storage unit 16. For example, it is possible to configure the present embodiment so that the ultrasound diagnosis apparatus is provided with a storage unit for storing therein the ultrasound image data acquired according to the setting information. Alternatively, for example, it is also possible to configure the present embodiment so that a storage unit for storing therein the ultrasound image data acquired according to the setting information is provided in an external apparatus other than the ultrasound diagnosis apparatus.

Figure 10:
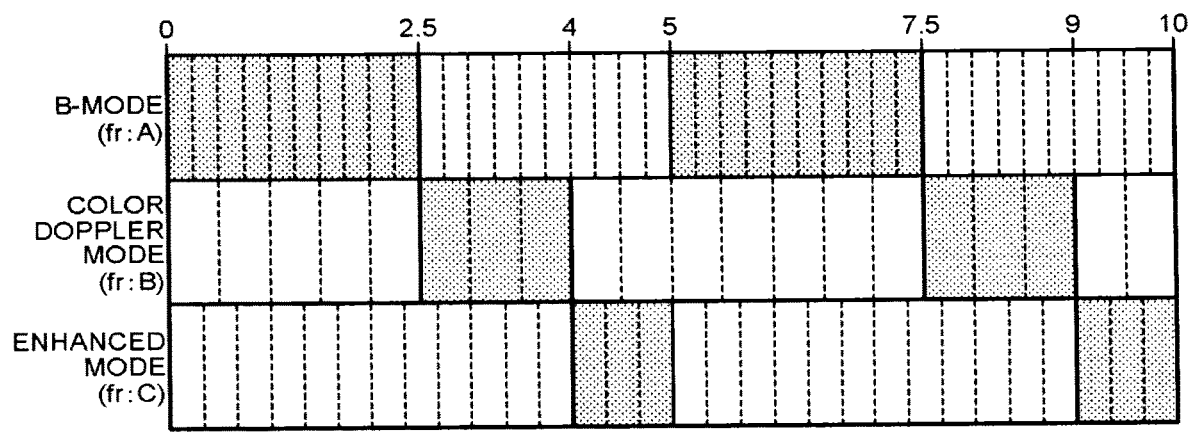
Figure 11:
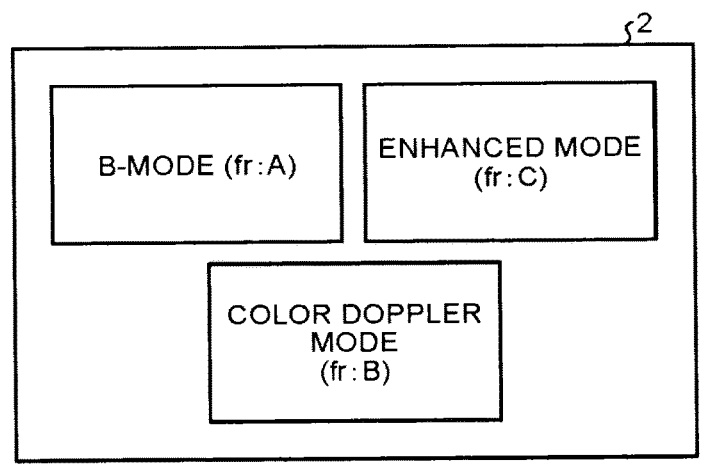

Further, as explained above, together with the storage control, the controlling unit 17 exercises control so that the monitor 2 displays the plurality of types of ultrasound image data generated by the image generating unit 14, according to the percentage set in the setting information. More specifically, the controlling unit 17 exercises display control as described below. FIGS. 9 to 11 are drawings of examples of display control according to the present embodiment.

According to a first display control method, the controlling unit 17 causes the plurality of types of ultrasound image data generated by the image generating unit 14 to be displayed as a moving picture in mutually the same display region of the monitor 2, by switching between the types of ultrasound image data to be displayed according to the percentage (the percentage of time periods) set in the setting information. More specifically, the controlling unit 17 switches between the types of ultrasound image data to be displayed in mutually the same display region, on the basis of the percentage set in the setting information, and switches between the times of generation of the ultrasound image data to be displayed in mutually the same display region, on the basis of display times according to frequency of generation.

For example, when the display plan (the unit time period: ten seconds) shown in FIG. 5A is set, under the control of the controlling unit 17, the monitor 2 displays, as illustrated in FIG. 9, the image data in the B-mode as a moving picture at frame rate "A" for five seconds, and subsequently displays the image data in the color Doppler mode as a moving picture at frame rate "B" for three seconds, and further displays the image data in the enhanced mode as a moving picture at frame rate "C" for two seconds.

After that, as illustrated in FIG. 9, under the control of the controlling unit 17, when the moving picture in the enhanced mode has finished being displayed, the monitor 2 switches from the enhanced mode to the B-mode again and displays moving pictures while switching between the modes in the order of "the B-mode, the color Doppler mode, and the enhanced mode".

In this situation, the first display control method is applicable both to a situation where the first image generation control method is implemented and to a situation where the second image generation control method is implemented. When the first display control method is implemented with the first image generation control method, the controlling unit 17 exercises control so that the pieces of ultrasound image data generated by the image generating unit 14 are displayed on the monitor 2 in the order of generation. For example, when the first image generation control method shown in FIG. 6A is implemented according to the display plan shown in FIG. 5A, the controlling unit 17 causes the monitor 2 to display, in the order of generation, the group of pieces of ultrasound image data generated by the image generating unit 14 along the time series while switching between the modes.

Alternatively, when the first display control method is implemented with the second image generation control method, the controlling unit 17 sequentially selects, from among the plurality of types of ultrasound image data generated in parallel to one another by the image generating unit 14, one of the types of ultrasound image data corresponding to the percentage set in the setting information and to the time of generation relevant to the display time according to the frequency of generation. After that, the controlling unit 17 exercises control so that the selected types of ultrasound image data are sequentially displayed on the monitor 2. For example, let us discuss an example in which the image generating unit 14 has generated a group of pieces of ultrasound image data in a plurality of modes in parallel to one another along a time series, by implementing the second image generation control method shown in FIG. 6B according to the display plan shown in FIG. 5C.

In that situation, as illustrated in FIG. 10, "for the duration of two and a half seconds from the start of the generation to 2.5 seconds", the controlling unit 17 selects the image data in the B-mode generated at frame rate "A" along the time series and causes the monitor 2 to display the selected image data. After that, as illustrated in FIG. 10, "for the duration of one and a half seconds from 2.5 seconds to 4 seconds", the controlling unit 17 selects the image data in the color Doppler mode generated at frame rate "B" along the time series and causes the monitor 2 to display the selected image data. After that, as illustrated in FIG. 10, "for the duration of one second from 4 seconds to 5 seconds", the controlling unit 17 selects the image data in the enhanced mode generated at frame rate "C" along the time series and causes the monitor 2 to display the selected image data.

Further, as illustrated in FIG. 10, "for the duration of two and a half seconds from 5 seconds to 7.5 seconds", the controlling unit 17 selects the image data in the B-mode generated at frame rate "A" along the time series and causes the monitor 2 to display the selected image data. After that, as illustrated in FIG. 10, "for the duration of one and a half seconds from 7.5 seconds to 9 seconds", the controlling unit 17 selects the image data in the color Doppler mode generated at frame rate "B" along the time series and causes the monitor 2 to display the selected image data. After that, as illustrated in FIG. 10, "for the duration of one second from 9 seconds to 10 seconds", the controlling unit 17 selects the image data in the enhanced mode generated at frame rate "C" along the time series and causes the monitor 2 to display the selected image data. The controlling unit 17 repeats the display control illustrated in FIG. 10 until an acquisition ending request is received.

In this situation, the controlling unit 17 performs the display control implementing the first display control method, in parallel to the storage control implementing the first storage control method or the second storage control method. It should be noted, however, that the controlling unit 17 may implement the first display control method, after exercising the storage control by implementing the first storage control method or the second storage control method. In that situation, the controlling unit 17 reads the image data from the internal storage unit 16 and implements the first display control method, in response to a display request made by the operator after the acquisition of the image data.

Alternatively, according to a second display control method, to each of a plurality of display regions of the monitor 2, the controlling unit 17 assigns a different one of the types of ultrasound image data to be displayed thereon. After that, the controlling unit 17 causes the plurality of types of ultrasound image data generated by the image generating unit 14 to be displayed as moving pictures in the plurality of display regions, respectively, while being arranged side by side and being separated according to the types thereof. More specifically, the controlling unit 17 switches between the times of generation of the ultrasound image data to be displayed in each of the plurality of display regions, on the basis of the display times according to the frequency of generation.

For example, when one of the display plans shown in FIGS. 5A, 5B, and 5C is set, the controlling unit 17 divides, as illustrated in FIG. 11, the display region of the monitor 2 into three sectional regions such as a B-mode display region, a color Doppler mode display region, and an enhanced mode display region. After that, as shown in FIG. 11, the monitor 2 displays the B-mode image data at frame rate "A" in the B-mode display region, displays the color Doppler image data at frame rate "B" in the color Doppler mode display region, and displays the calcification enhanced image data at frame rate "C" in the enhanced mode display region.

In this situation, the second display control method is applicable to both a situation where the first image generation control method is implemented and a situation where the second image generation control method is implemented. When the second display control method is implemented with the first image generation control method, the controlling unit 17 assigns the ultrasound image data generated by the image generating unit 14 while switching between the modes according to the display plan, to a corresponding display region according to the type thereof so that each type of ultrasound image data is displayed in the order of generation. In this situation, according to the first image generation control method, there are time periods during which no display-purpose frame is present in each of the modes, i.e., time periods during which it is not possible to display any image data (hereinafter, a "display disabled time period"). During each display disabled time period, the controlling unit 17 displays a frame that was displayed immediately prior to the display disabled time period as a still picture or displays a frame in black only.

Alternatively, when the second display control method is implemented with the second image generation control method, the controlling unit 17 sequentially selects, from among the plurality of types of ultrasound image data generated in parallel to one another by the image generating unit 14, one of the types of ultrasound image data corresponding to the percentage set in the setting information and to the time of generation relevant to the display time according to the frequency of generation. After that, the controlling unit 17 exercises control so that each of the selected types of ultrasound image data is displayed in one of the display regions of the monitor 2 corresponding to the type thereof.

When the image data is generated by implementing the second image generation control method, although there are display-purpose frames even in the display disabled time periods described above, the controlling unit 17 displays a frame that was displayed immediately prior as a still picture or displays a frame in black only, during each time period corresponding to a display disabled time period according to the display plan. Alternatively, when the second display control method is implemented with the second image generation control method, the controlling unit 17 may cause all of the plurality of types of ultrasound image data generated in parallel to one another by the image generating unit 14 to be displayed side by side as moving pictures, so as to prioritize displaying all of the types of ultrasound image data set in the setting information.

In this situation, the controlling unit 17 implements the second display control method in parallel to the storage control implementing the first storage control method or the second storage control method. It should be noted, however, that the controlling unit 17 may implement the second display control method, after exercising the storage control by implementing the first storage control method or the second storage control method. In that situation, the controlling unit 17 reads the image data from the internal storage unit 16 and implements the second display control method, in response to a display request made by the operator after the acquisition of the image data.

When implementing the second display control method after the data has been stored, the controlling unit 17 may skip the display disabled time period described above and may cause the plurality of types of ultrasound image data to be displayed side by side as moving pictures.

Further, when the third image generation control method has been implemented, the controlling unit 17 reads the image data from the internal storage unit 16 and implements the first display control method or the second display control method, in response to a display request made by the operator after the acquisition of the image data. Alternatively, when the third image generation control method has been implemented, the controlling unit 17 may implement, in a real-time manner, the first display control method or the second display control method on the group of pieces of ultrasound image data generated by implementing the first image generation control method.

Any of the image generation control methods, the storage control methods, and the display control methods described above may be specified by the operator or may be specified in advance as an initial setting.

Figure 12:
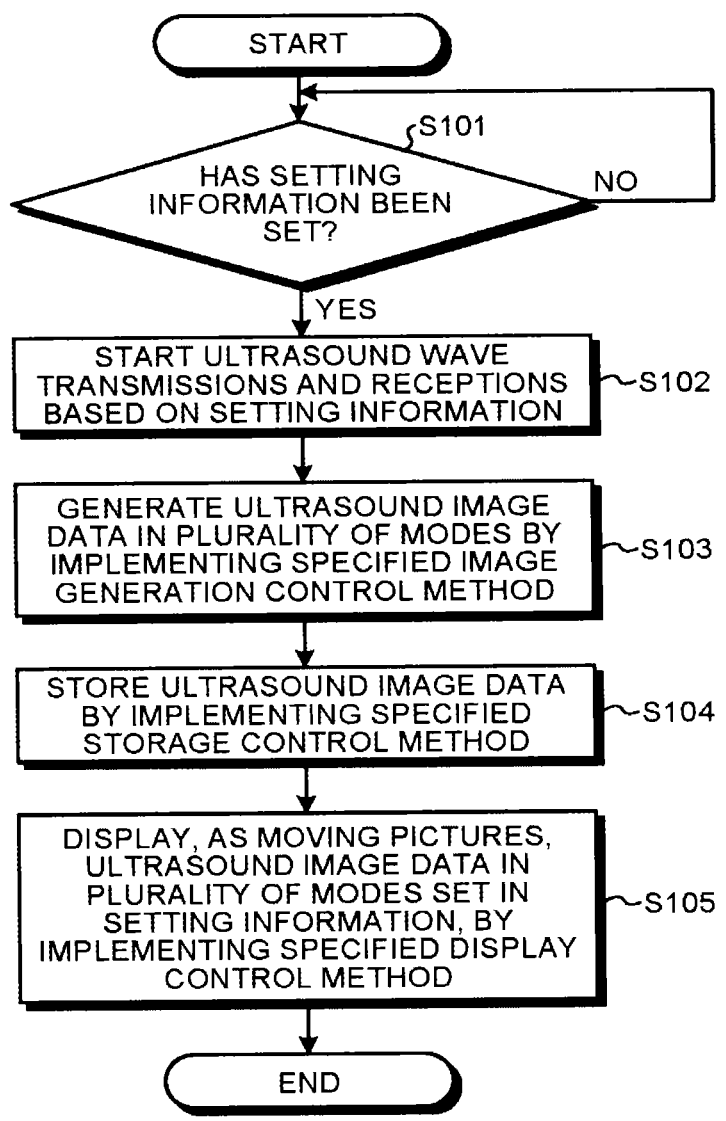
FIG. 12 is a flowchart of an exemplary process performed by the ultrasound diagnosis apparatus according to the present embodiment.

Next, an exemplary process performed by the ultrasound diagnosis apparatus according to the present embodiment will be explained, with reference to FIG. 12. FIG. 12 is a flowchart of the exemplary process performed by the ultrasound diagnosis apparatus according to the present embodiment. The flowchart in FIG. 12 illustrates an example in which the storage control and the display control are performed in a real-time manner.

As illustrated in FIG. 12, the obtaining unit 18 included in the ultrasound diagnosis apparatus according to the present embodiment judges whether setting information has been set (step S101). In this situation, if no setting information has been set (step S101: No), the obtaining unit 18 stands by until setting information is set.

On the contrary, if setting information has been set (step S101: Yes), the obtaining unit 18 obtains the setting information and notifies the controlling unit 17 of the obtained setting information. After that, by controlling the ultrasound probe 1 via the transmitting and receiving unit 11, the controlling unit 17 causes ultrasound wave transmissions and receptions based on the setting information to start (step S102). For example, the controlling unit 17 sets a display plan on the basis of the setting information and causes ultrasound wave transmissions and receptions based on the display plan to start.

After that, according to an instruction from the controlling unit 17, the image generating unit 14 generates ultrasound image data in a plurality of modes specified in the setting information, by implementing the specified image generation control method (step S103).

Subsequently, according to an instruction from the controlling unit 17, the image generating unit 14 stores the ultrasound image data into the internal storage unit 16, by implementing the specified storage control method (step S104).

After that, according to an instruction from the controlling unit 17, the monitor 2 displays, as moving pictures, the ultrasound image data in the plurality of modes set in the setting information, by implementing the specified display control method (step S105), and the process is thus ended. The flowchart in FIG. 12 illustrates an example in which the data acquisition is completed in one unit time period. If the data acquisition is performed for a time period longer than one unit time period, the ultrasound diagnosis apparatus repeats the process at steps S103 through S105 until an acquisition ending request is received. The flowchart illustrated in FIG. 12 is also applicable to a situation where, during a data acquisition time period that lasts for a plurality of unit time periods, the operator changes at least one selected from the image generation control method, the storage control method, and the display control method.

As explained above, according to the present embodiment, the ultrasound diagnosis apparatus automatically acquires the ultrasound image data in the plurality of modes based on the setting information and causes the acquired ultrasound image data in the plurality of modes to be automatically displayed side by side or to be displayed while the mode is automatically switched from one to another. Further, according to the present embodiment, the ultrasound diagnosis apparatus automatically stores therein the ultrasound image data in the plurality of modes acquired on the basis of the setting information, in such a manner that it is possible to read the ultrasound image data even after the data is acquired. In other words, according to the present embodiment, the operator or a medical doctor is able to collectively and easily obtain the information required to make a diagnosis from the ultrasound examination, only by inputting the setting information to the ultrasound diagnosis apparatus, the setting information indicating the plurality of modes required by the ultrasound examination performed on the subject P and the percentage that is set in relation to the display for each of the modes. Further, according to the present embodiment, it is possible to prevent the situation where the ultrasound image data taking processes in the modes that are necessary are missing from the procedure.

Figure 13A:
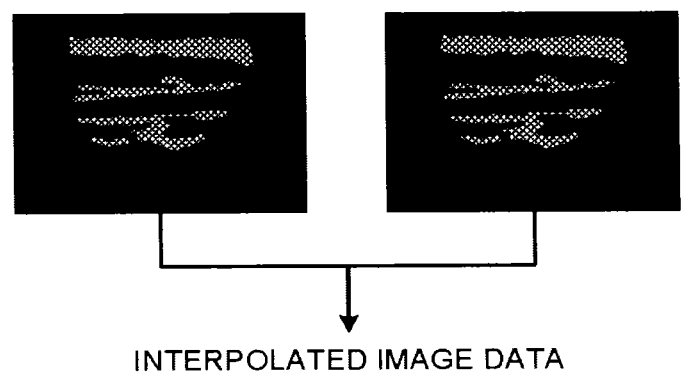
FIG. 13A is a drawing for explaining a first modification example of the present embodiment.
Figure 13B:
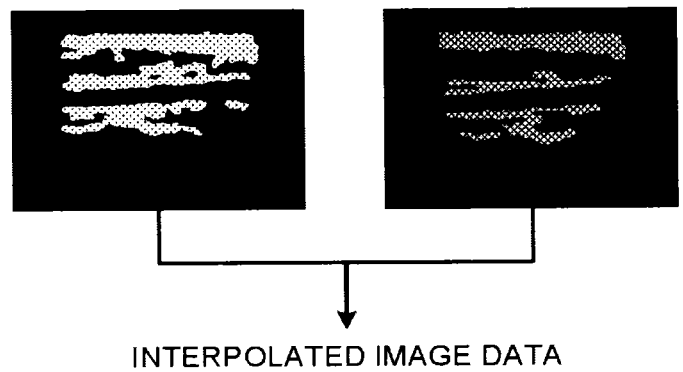
FIG. 13B is a drawing for explaining a second modification example of the present embodiment.
Figure 15:
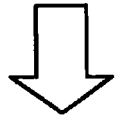
FIG. 15 is a drawing for explaining a fourth modification example of the present embodiment.

The ultrasound diagnosis apparatus according to the present embodiment may be used in modification examples described below. Modification examples of the present embodiment will be explained below, with reference to FIGS. 13A, 13B, 14A, 14B, and 15. FIG. 13A is a drawing for explaining a first modification example of the present embodiment. FIG. 13B is a drawing for explaining a second modification example. FIGS. 14A and 14B are drawings for explaining a third modification example of the present embodiment. FIG. 15 is a drawing for explaining a fourth modification example of the present embodiment.

For example, the frame rate of the calcification enhanced image data is lower than the frame rate of the B-mode image data, because the former has a larger processing amount. For this reason, for example, according to the first display control method, when the mode is switched from the B-mode to the enhanced mode, because the frame rate suddenly drops, the viewer who is viewing the image data feels strange. In another example, according to the second display control method, because the frame rates are different between the B-mode display region and the enhanced mode display region, the viewer who is viewing the image data feels strange.

To cope with these situations, according to the first modification example, with respect to pieces of ultrasound image data of mutually the same type to be displayed on the monitor 2, if no such ultrasound image data is present that corresponds to the time of generation relevant to the display time according to predetermined display frequency, the controlling unit 17 exercises control so that interpolated image data generated by performing an interpolating process on the two frames displayed before and after the display time is displayed as the display-purpose image data.

For example, the controlling unit 17 selects the two pieces of calcification enhanced image data to be displayed before and after the display time according to the frame rate of the B-mode image data. After that, for example, under the control of the controlling unit 17, the image generating unit 14 generates, as illustrated in FIG. 13A, interpolated image data by calculating an arithmetic mean of the two pieces of calcification enhanced image data selected by the controlling unit 17. Further, the controlling unit 17 causes the interpolated image data generated by the image generating unit 14 to be displayed between the times at which the two pieces of calcification enhanced image data are displayed. The interpolating process between two pieces of image data in mutually the same mode may be realized with a motion correction, instead of with an arithmetic mean.

Alternatively, according to the first display control method, for example, when the mode is switched from the B-mode to the enhanced mode, because the B-mode image data in black and white is switched to the calcification enhanced image data in which white dots are rendered on a blue-color system background, the viewer who is viewing the image data feels strange.

To cope with this situation, according to the second modification example, the controlling unit 17 exercises control so as to display, as the display-purpose image data for a time period when the switching occurs between the types of ultrasound image data to be displayed on the monitor 2, interpolated image data generated by performing an interpolating process on the two frames displayed before and after the time at which the switching occurs.

For example, under the control of the controlling unit 17, the image generating unit 14 generates, as illustrated in FIG. 13B, interpolated image data by calculating an arithmetic mean of the last frame of the B-mode image data and the first frame of the calcification enhanced image data. Further, the controlling unit 17 causes the interpolated image data generated by the image generating unit 14 to be displayed for the time period when the B-mode is switched to the enhanced mode.

By implementing the first modification example and the second modification example, it is possible to reduce the strange feeling that the viewer may experience when viewing the group of pieces of ultrasound image data that is displayed as a moving picture on the basis of the setting information.

Further, the exemplary embodiment described above may be configured so that the setting information set by the operator is modified. In that situation, as the third modification example, if the setting information has been modified, the controlling unit 17 exercises display control based on the modified setting information. Further, the third modification example is applicable to both a situation where the setting information is modified during the data acquisition and a situation where the setting information is modified after the data acquisition.

The third modification example will further be explained, by using exemplary setting information illustrated in FIG. 14A. For example, as illustrated in FIG. 14A, the operator sets four types of ultrasound image data, namely, ultrasound image data in the B-mode, in the color Doppler mode, in the elastography mode, and in the enhanced mode, as the display-purpose image data. After that, for example, the operator sets, as illustrated in FIG. 14A, the percentage to display the B-mode image data is "40%", the percentage to display the color Doppler mode is "20%", the percentage to display the elasticity image data in the elastography mode is "20%", and the percentage to display the calcification enhanced image data in the enhanced mode is "20%".

For example, if the operator has modified the setting information during the data acquisition, so as to indicate that the enhanced mode will not be executed, the controlling unit 17 modifies the setting information shown in FIG. 14A to setting information shown in FIG. 14B where the three types of ultrasound image data, namely, the ultrasound image data in the B-mode, in the color Doppler mode, and in the elastography mode are set as the display-purpose image data. After that, the controlling unit 17 modifies the setting information shown in FIG. 14A to the setting information shown in FIG. 14B indicating that the percentage to display the B-mode image data is "50%", the percentage to display the color Doppler mode image data is "25%", and the percentage to display the elasticity image data in the elastography mode is "25%". In the example shown in FIG. 14B, the controlling unit 17 has calculated the percentage of display time periods for the B-mode, the color Doppler mode, and the elastography mode in the modified setting information, while maintaining the ratio (40%:20%:20%=2:1:1) of the percentage values of the display time periods for the B-mode, the color Doppler mode, and the elastography mode in the initial setting information. In this situation, during the data acquisition, together with the process of selecting image taking modes, the operator may also change the percentage of display time periods for the selected image taking modes. For example, the operator may change the percentage of display time periods for "the B-mode, the color Doppler mode, and the elastography mode" to "50%, 30%, and 20%".

Further, on the basis of the modified setting information shown in FIG. 14B, the controlling unit 17 exercises the display control according to the display control method specified by the operator, during the data acquisition. In this situation, together with the process of modifying the setting information, the operator may modify one or more selected from the display control method, the image generation control method, the storage control method, and the display control method that are specified in the initial setting information.

Alternatively, the controlling unit 17 may perform the processes described above after the data acquisition. In that situation, the controlling unit 17 resets the setting information shown in FIG. 14B on the basis of the image taking modes selected by the operator, after the data acquisition. Further, the controlling unit 17 exercises the display control according to the display control method specified by the operator by using the setting information shown in FIG. 14B and the group of pieces of data that has already been stored in the internal storage unit 16. In this situation, if image taking modes are selected after the data acquisition, and also, the data acquisition was performed by implementing the first image generation control method, the controlling unit 17 resets the percentage of display time periods for the selected image taking modes, by using the ratio of the percentage values of the display time periods for the image taking modes that were set in the initial setting information (see FIG. 14B). If image taking modes are selected after the data acquisition was performed by implementing the second image generation control method, the operator is able to set the percentage of display time periods for the selected image taking modes to arbitrary values. In the third modification example, for instance, the operator collectively performs, according to the initial setting information, image taking processes in a plurality of image taking modes that have a possibility of being used in an image diagnosis. Then, according to the third modification example, the operator selects two or more of the image taking modes that are required to make an image diagnosis by referring to the monitor 2, during the data acquisition or after the data acquisition. It is therefore possible to efficiently make the image diagnosis, by using the ultrasound image data in each of the selected plurality of image taking modes.

In the third modification example, it is also possible to add one or more image taking modes during the data acquisition. For example, in the third modification example, the setting information shown in FIG. 4 may be modified, during the data acquisition, to the setting information shown in FIG. 14A, by adding the elastography mode. In that situation, the controlling unit 17 exercises display control by using the modified setting information shown in FIG. 14A and the display control method specified by the operator during the data acquisition. In the present third modification example, by referring to the monitor 2 during the data acquisition, the operator adds, at that time, one or more image taking modes required to make an image diagnosis. It is therefore possible to efficiently make the image diagnosis, by using the ultrasound image data in each of the plurality of image taking modes including the added image taking modes.

Further, during an image diagnosis process, together with the ultrasound image data of an observation target of the subject P, a medical doctor may wish to view medical image data of the same observation target of the subject P that was taken by other medical image diagnosis apparatuses (e.g., an X-ray Computed Tomography (CT) apparatus and a Magnetic Resonance Imaging (MRI) apparatus).

To cope with this situation, in the fourth modification example, the obtaining unit 18 obtains setting information in which a plurality of types of medical image data are set as the display-purpose image data and in which the percentage for displaying each of the types of medical image data is set. Further, the controlling unit 17 exercises control so that the plurality of types of medical image data set in the setting information are displayed as a moving picture in mutually the same display region of the display unit, by switching between the types of medical image data to be displayed according to the percentage set in the setting information.

In other words, in the fourth modification example, the controlling unit 17 implements the first display control method while using the mutually-different plurality of types of medical image data as display targets. More specifically, the controlling unit 17 sequentially selects, from among the plurality of types of medical image data that are generated along a time series and according to the frequency set in advance for each of the types, one of the types of medical image data corresponding to the percentage specified in the setting information and to the time of generation relevant to the display time according to the frequency of generation.

After that, the controlling unit 17 exercises control so that the selected types of medical image data are sequentially displayed on the monitor.

For example, as shown in FIG. 15, the operator sets three types of medical image data, namely, ultrasound image data, X-ray CT image data, and MRI image data as the display-purpose image data. After that, for example, the operator sets percentage values indicating that, as shown in FIG. 15, the percentage to display the ultrasound image data is "50%", the percentage to display the X-ray CT image data is "30%", and the percentage to display the MRI image data is "20%". By referring to the received setting information, the controlling unit 17 receives the X-ray CT image data and the MRI image data obtained by taking images of an observation site of the subject P, front an X-ray CT apparatus and an MRI apparatus or from a Picture Archiving and Communication System (PACS) database or a database of an electronic medical record system.

After that, the controlling unit 17 sets a display plan on the basis of the setting information. Subsequently, under the control of the controlling unit 17, the monitor 2 excises a display according to the first display control method. For example, as shown in FIG. 15, the monitor 2 displays the ultrasound image data as a moving picture at frame rate "U" for five seconds, and subsequently displays the X-ray CT image data as a moving picture at frame rate "X" for three seconds, and then displays the MRI image data as a moving picture at frame rate "M" for two seconds. According to the fourth modification example, it is possible to collectively and easily obtain the information required to make a diagnosis from the medical examination using the plurality of types of medical image data.

Similarly to the third modification example, if the setting information has been modified, the controlling unit 17 may exercise the display control on the basis of the modified setting information, also in the fourth modification example. For example, let us discuss a situation where the types of display-purpose image data are changed to ultrasound image data and X-ray CT image data, and also, the percentage to display the ultrasound image data is changed to "70%", whereas the percentage to display the X-ray CT image data is changed to "30%". In that situation, under display control of the controlling unit 17, the monitor 2 displays the ultrasound image data as a moving picture at frame rate "U" for seven seconds, and subsequently displays the X-ray CT image data as a moving picture at frame rate "X" for three seconds.

The image processing method explained in the fourth modification example may be implemented by other medical image diagnosis apparatuses besides the ultrasound diagnosis apparatus. Further, the image processing method explained in the fourth modification example may be implemented by an image processing apparatus that is capable of obtaining a plurality of types of medical image data from a database storing therein medical image data.

The constituent elements of the apparatuses that are shown in the drawings in relation to the description of the exemplary embodiments and the modification examples are based on functional concepts. Thus, it is not necessary to physically configure the elements as indicated in the drawings. In other words, the specific mode of distribution and integration of the apparatuses is not limited to the ones shown in the drawings. It is acceptable to functionally or physically distribute or integrate all or a part of the apparatuses in any arbitrary units, depending on various loads and the status of use. For example, the B-mode processing unit 12 and the Doppler processing unit 13 may be integrated together as a signal processing unit. Alternatively, the B-mode processing unit 12, the Doppler processing unit 13, and the image generating unit 14 may be integrated together as an image generation processing unit. Further, all or an arbitrary part of the processing functions performed by the apparatuses may be realized by a Central Processing Unit (CPU) and a computer program that is analyzed and executed by the CPU or may be realized as hardware using wired logic.

Further, the image processing methods described in the exemplary embodiments and the modification examples may be realized by causing a computer such as a personal computer or a workstation to execute an image processing computer program (hereinafter, the "image processing program") prepared in advance. The image processing program may be distributed via a network such as the Internet. Furthermore, it is also possible to record the image processing program onto a computer-readable non-transitory recording medium such as a hard disk, a flexible disk (FD), a Compact Disk Read-Only Memory (CD-ROM), a Magneto-optical (MO) disk, a Digital Versatile Disk (DVD), or a flash memory such as a Universal Serial Bus (USB) memory or a Secure Digital (SD) card memory, so that a computer is able to read the image processing program from the non-transitory recording medium and to execute the read image processing program.

As explained above, according to at least one aspect of the exemplary embodiments and the modification examples, it is possible to collectively and easily obtain the information required to make a diagnosis from the ultrasound examination.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
obtaining circuitry that obtains setting information in which a plurality of types of ultrasound image data are set as display-purpose image data and in which a percentage of a time period to display the display-purpose image data is set for each of the plurality of types;
image generating circuitry that generates, along a time series, each of the plurality of types of ultrasound image data set in the setting information; and
controlling circuitry that exercises control to repeat a processing of switching and displaying the plurality of types of ultrasound image data on a display in a sequential order according to the percentage set in the setting information, wherein
when the controlling circuitry receives a modification of the setting information such that at least one type among the plurality of types of ultrasound image data set in the setting information is deleted, the controlling circuitry modifies the setting information such that a ratio of, among the percentage of the time period of the plurality of types, a percentage of a time period of a plurality of types other than the at least one type in the setting information before modification is maintained, and exercises display control based on the modified setting information.

2. The ultrasound diagnosis apparatus according to claim 1, wherein the plurality of types of ultrasound image data set in the setting information include a plurality of types of ultrasound image data that are generatable from data which is generated by performing a B-mode processing process on reflected-wave signals.

3. The ultrasound diagnosis apparatus according to claim 2, wherein
the plurality of types of ultrasound image data set in the setting information as the display-purpose image data are each a type of ultrasound image data which the image generating circuitry is configured to generate from data obtained by performing at least one of the following processes on the reflected-wave signal signals: a signal amplitude feature extraction process, an intensity feature extraction process, a frequency feature extraction process, a spatial correlation feature extraction process, and a temporal correlation feature extraction process, and
the signal processing processes of mutually the same type are signal processing processes including the intensity feature extraction process.

4. The ultrasound diagnosis apparatus according to claim 1, wherein
the image generating circuitry generates the plurality of types of ultrasound image data set in the setting information in parallel to one another, along the time series and according to frequency set for each of the types,
the controlling circuitry sequentially selects, from among the plurality of types of ultrasound image data generated in parallel to one another by the image generating circuitry, one of the types of ultrasound image data corresponding to the percentage set in the setting information and to a time of generation relevant to a display time according to frequency of generation, and
the controlling circuitry further exercises control so that the selected types of ultrasound image data are sequentially displayed on the display.

5. The ultrasound diagnosis apparatus according to claim 1, wherein
the image generating circuitry generates each of the plurality of types of ultrasound image data set in the setting information along the time series and according to frequency set for the type, while sequentially switching between the types of ultrasound image data to have a generating process performed thereon according to the percentage set in the setting information, and
the controlling circuitry exercises control so that the ultrasound image data generated by the image generating circuitry is displayed on the display in an order of generation.

6. The ultrasound diagnosis apparatus according to claim 1, wherein the controlling circuitry exercises control so that, to each of a plurality of storage areas of a memory, a different one of the plurality of types of ultrasound image data generated by the image generating circuitry is assigned and stored therein in an order of generation.

7. The ultrasound diagnosis apparatus according to claim 1, wherein the controlling circuitry exercises control so that the plurality of types of ultrasound image data generated by the image generating circuitry are stored into a mutually same storage area of a memory in an order of generation.

8. The ultrasound diagnosis apparatus according to claim 1, wherein, the controlling circuitry exercises control so as to display, as display-purpose image data for a time period when the switching occurs between the types of ultrasound image data to be displayed on the display, interpolated image data generated by performing an interpolating process on two frames displayed before and after a time at which the switching occurs.

9. The ultrasound diagnosis apparatus according to claim 1, wherein, when the setting information has been modified, the controlling circuitry exercises display control based on the modified setting information.

10. The ultrasound diagnosis apparatus according to claim 1, wherein the percentage of the time period corresponds to a length of time to display the display-purpose image data, the percentage of the time period being different for different types of image data.

11. The ultrasound diagnosis apparatus according to claim 10, wherein the obtaining circuitry receives input of the percentage of the time period to display the display-purpose image data set for each of the plurality of types, such that a percentage of B-mode image data is set at 50%, a percentage of color Doppler mode image data is set at 30%, and a percentage of calcification enhanced image data is set at 20%.

12. An image processing apparatus comprising:
obtaining circuitry that obtains setting information in which a plurality of types of medical image data are set as display-purpose image data and in which a percentage of a time period for displaying each of the plurality of types of medical image data is set for each of the plurality of the types; and
controlling circuitry that exercises control to repeat a processing of switching and displaying the plurality of types of medical image data on a display in a sequential order according to the percentage set in the setting information, wherein;
when the controlling circuitry receives a modification of the setting information such that at least one type among the plurality of types of ultrasound image data set in the setting information is deleted, the controlling circuitry modifies the setting information such that a ratio of, among the percentage of the time period of the plurality of types, a percentage of a time period of a plurality of types other than the at least one type in the setting information before modification is maintained, and exercises display control based on the modified setting information.

13. The image processing apparatus according to claim 12, wherein
the controlling circuitry sequentially selects, from among the plurality of types of medical image data that are generated along a time series and according to frequency set in advance for each of the types, one of the types of medical image data corresponding to the percentage specified in the setting information and to a time of generation relevant to a display time according to frequency of generation, and
the controlling circuitry further exercises control so that the selected types of medical image data are sequentially displayed on the display.

14. The image processing apparatus according to claim 12, wherein, when the setting information has been modified, the controlling circuitry exercises display control based on the modified setting information.

* * * * *